(12) United States Patent
Branton et al.

(10) Patent No.: US 11,035,847 B2
(45) Date of Patent: Jun. 15, 2021

(54) DETERMINISTIC STEPPING OF POLYMERS THROUGH A NANOPORE

(71) Applicant: President and Fellows of Harvard College, Cambridge, MA (US)

(72) Inventors: Daniel Branton, Lexington, MA (US); Stephen Jordan Fleming, Cambridge, MA (US); Jene A. Golovchenko, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 290 days.

(21) Appl. No.: 16/022,594

(22) Filed: Jun. 28, 2018

(65) Prior Publication Data

US 2019/0004029 A1 Jan. 3, 2019

Related U.S. Application Data

(60) Provisional application No. 62/526,823, filed on Jun. 29, 2017.

(51) Int. Cl.

| | | |
|---|---|---|
| G01N 33/487 | (2006.01) | |
| B01D 71/02 | (2006.01) | |
| B01D 71/74 | (2006.01) | |
| C12Q 1/6869 | (2018.01) | |
| G01N 27/40 | (2006.01) | |
| B82Y 35/00 | (2011.01) | |

(52) U.S. Cl.
CPC ..... *G01N 33/48721* (2013.01); *B01D 71/021* (2013.01); *B01D 71/74* (2013.01); *C12Q 1/6869* (2013.01); *G01N 27/40* (2013.01); *B82Y 35/00* (2013.01); *C12Y 306/01039* (2013.01)

(58) Field of Classification Search
None
See application file for complete search history.

(56) References Cited

U.S. PATENT DOCUMENTS

| | | | |
|---|---|---|---|
| 5,795,782 A | 8/1998 | Church et al. | |
| 6,627,067 B1 | 9/2003 | Branton et al. | |
| 7,189,503 B2 | 3/2007 | Akeson et al. | |
| 7,238,485 B2 | 7/2007 | Akeson et al. | |
| 7,468,271 B2 | 12/2008 | Golovchenko et al. | |
| 7,744,816 B2 | 6/2010 | Su et al. | |
| 7,947,454 B2 * | 5/2011 | Akeson | B82Y 30/00 435/6.12 |
| 8,273,532 B2 | 9/2012 | Gershow et al. | |
| 8,698,481 B2 | 4/2014 | Lieber et al. | |
| 9,274,097 B2 | 3/2016 | Golovchenko et al. | |
| 9,617,591 B2 | 4/2017 | Moysey et al. | |
| 9,702,849 B2 | 7/2017 | Lieber et al. | |
| 9,815,082 B2 | 11/2017 | Golovchenko et al. | |
| 2004/0055875 A1 | 3/2004 | Siwy et al. | |
| 2012/0234679 A1 | 9/2012 | Garaj et al. | |
| 2014/0335512 A1 | 11/2014 | Moysey et al. | |
| 2015/0060276 A1 | 3/2015 | Golovchenko et al. | |
| 2015/0060277 A1 | 3/2015 | Golovchenko et al. | |
| 2016/0231307 A1 | 8/2016 | Xie | |
| 2018/0148481 A2 | 5/2018 | Howorka et al. | |

FOREIGN PATENT DOCUMENTS

| | | |
|---|---|---|
| CN | 102445480 A | 5/2012 |
| CN | 102590314 A | 7/2012 |
| EP | 1441213 | 7/2004 |
| EP | 1443318 | 8/2004 |
| WO | 2004028673 | 4/2004 |

OTHER PUBLICATIONS

Deamer, et al. (2015) "Three decades of nanopore sequencing", Nature Biotechnology, 34(5): 518-524. (Year: 2015).*
Manrao, et al. (2012) "Reading DNA at single-nucleotide position with a mutant MspA nanopore and phi29 DNA polymerase", Nature Biotechnology, 30(4): 349-54. (Year: 2012).*
Laszlo, et al. (2014) "Decoding long nanopore sequencing reads of natural DNA", Nature Biotechnology, 32(8): 829-834. (Year: 2014).*
Shcreiber, et al. (2013) "Error rates for nanopore discrimination among cytosine, methylcytosine, and hydroxymethylcytosine along individual DNA strands", PNAS Early Edition, downloaded at http://pnas.org/cgi/doi/10.1073/pnas.1310615110, 6 pages long. (Year: 2013).*
PCT/US2018/040152, International Search Report, Form PCT/ISA/210 first sheet, second sheet, continuation of second sheet, and patent family annex sheet, dated Jan. 2019.
PCT/US2018/040152, Written Opinion of the International Searching Authority, Form PCT/ISA/237 cover sheet, sheets Box No. I-Box No. VIII, and Separate Sheet sheets 1-2, dated Jan. 2019.
Deamer et al., Three decades of nanopore sequencing, Nature Biotechnology, vol. 34, No. 5, pp. 518-524, May 2016.

(Continued)

*Primary Examiner* — Robert M Kelly

(74) *Attorney, Agent, or Firm* — Theresa A. Lober

(57) ABSTRACT

In a method p for controlling translocation of a target polymer molecule through a nanopore, a clamp is reversibly bound to a sequential plurality of polymer subunits along the target polymer molecule length and the molecule and clamp are disposed in an ionic solution that is in fluidic communication with the nanopore. A constant translocation force is applied across the nanopore to induce travel of the target polymer molecule into the nanopore, until the clamp abuts the nanopore aperture and stops further travel of the target polymer molecule into the nanopore. Then a voltage control pulse is applied across the nanopore and/or a thermal control pulse is applied at the nanopore, with a pulse duration that steps the clamp along the target polymer molecule by no more than one polymer subunit in a direction opposite that of travel into the nanopore. No fuel is provided to the clamp.

30 Claims, 14 Drawing Sheets

Specification includes a Sequence Listing.

(56) References Cited

OTHER PUBLICATIONS

Albertorio et al., "Base dependent DNA-carbon nanotube interactions: activation enthalpies and assembly-disassembly control," Nanotechnology, vol. 20, pp. 395101(1-9), Sep. 2009.

Bates et al., "Dynamics of DNA Molecules in a Membrane Channel Probed by Active Control Techniques," Biophysical Journal, vol. 84, pp. 2366-2372, Apr. 2003.

Fleming et al., Charge, Diffusion, and Current Fluctuations of Single-Stranded DNA Trapped in an MspA Nanopore, Biophysical Journal, vol. 112, pp. 368-375, Supplemental Information Cover sheet and pp. 1-7, Jan. 2017.

Lu et al., "Thermal Motion of DNA in an MspA Pore," Biophysical Journal, vol. 109, pp. 1439-1445, Oct. 2015.

Branton et al., "The potential and challenges of nanopore sequencing," Nat. Biotechnol. vol. 26, No. 10, pp. 1146-1153, Oct. 2008.

Cherf et al., "Automated forward and reverse ratcheting of DNA in a nanopore at 5-Å precision," Nature Biotechnology, vol. 30, No. 4, pp. 344-348, Apr. 2012.

Chu et al., "Real-Time Monitoring of DNA Polymerase Function and Stepwise Single-Nucleotide DNA Strand Translocation through a Protein Nanpore," Angew. Chem., vol. 122, pp. 10304-10307, Nov. 2010.

Fologea et al., "DNA conformation and base number simultaneously determined in a nanopore," Electrophoresis, vol. 28, pp. 3186-3192, 2007.

Meller, "Dynamics of polynucleotide transport through nanometre-scale pores," J. Phys.: Condens. Matter, vol. 15, pp. R581-R607, Apr. 2003.

Nakane et al., "A Nanosensor for Transmembrane Capture and Identification of Single Nucleic Acid Molecules," Biophysical Journal, vol. 87, pp. 615-621, Jul. 2004.

Zwolak et al., "Colloquium: Physical approaches to DNA sequencing and detection," Revs. of Modern Physics, vol. 80, pp. 141-165, Jan. 2008.

Baker et al., "ClpXP, an ATP-powered unfolding and protein-degradation machine," Biochimica et Biophysica Acta, vol. 1823, pp. 15-28, Jun. 2011.

Nivala et al., "Unfoldase-mediated protein translocation through an a-hemolysin nanopore," Nat. Biotechnol. vol. 31, No. 3, pp. 247-250, Mar. 2013.

Lieberman et al., "Processive Replication of Single DNA Molecules in a Nanopore Catalyzed by phi29 DNA Polymerase," J. Am. Chem. Soc., vol. 132, No. 50, pp. 17961-17972, Dec. 2010.

Lu et al., Control and Thermal Motion of DNA in an MspA Pore, NHGRI Advanced DNA Sequencing Technology Development Meeting, San Diego, CA, p. 1, May 2015.

Mulkidjanian et al., "Inventing the dynamo machine: the evolution of the F-type and V-type ATPases," Nature Reviews Microbiology, vol. 5, pp. 892-899, Nov. 2007.

Itoh et al., "Mechanically driven ATP synthesis by F1-ATPase," Nature, vol. 427, pp. 465-468, Jan. 2004.

Von Hippel et al., "A General Model for Nucleic Acid Helicases and Their 'Coupling' within Macromolecular Machines," Cell, vol. 104, No. 2, pp. 177-190, Jan. 2001.

Saikrishnan et al., "Mechanistic Basis of 5'-3' Translocation in SF1B Helicases," Cell, vol. 137, pp. 849-859, May 2009.

Langford et al., "Unsupported planar lipid membranes formed from mycolic acids of *Mycobacterium tuberculosis*," Jnl. of Lipid Research, vol. 52, pp. 272-277, Nov. 2010.

Zhao et al., "Triblock Copolymer Syntheses of Mesoporous Silica with Periodic 50 to 300 Angstrom Pores," Science, vol. 279, pp. 548-552, Jan. 1998.

Chinese Patent Application No. 201880056523.4, CNIPA Communication, six pages, dated Apr. 2, 2021.

\* cited by examiner

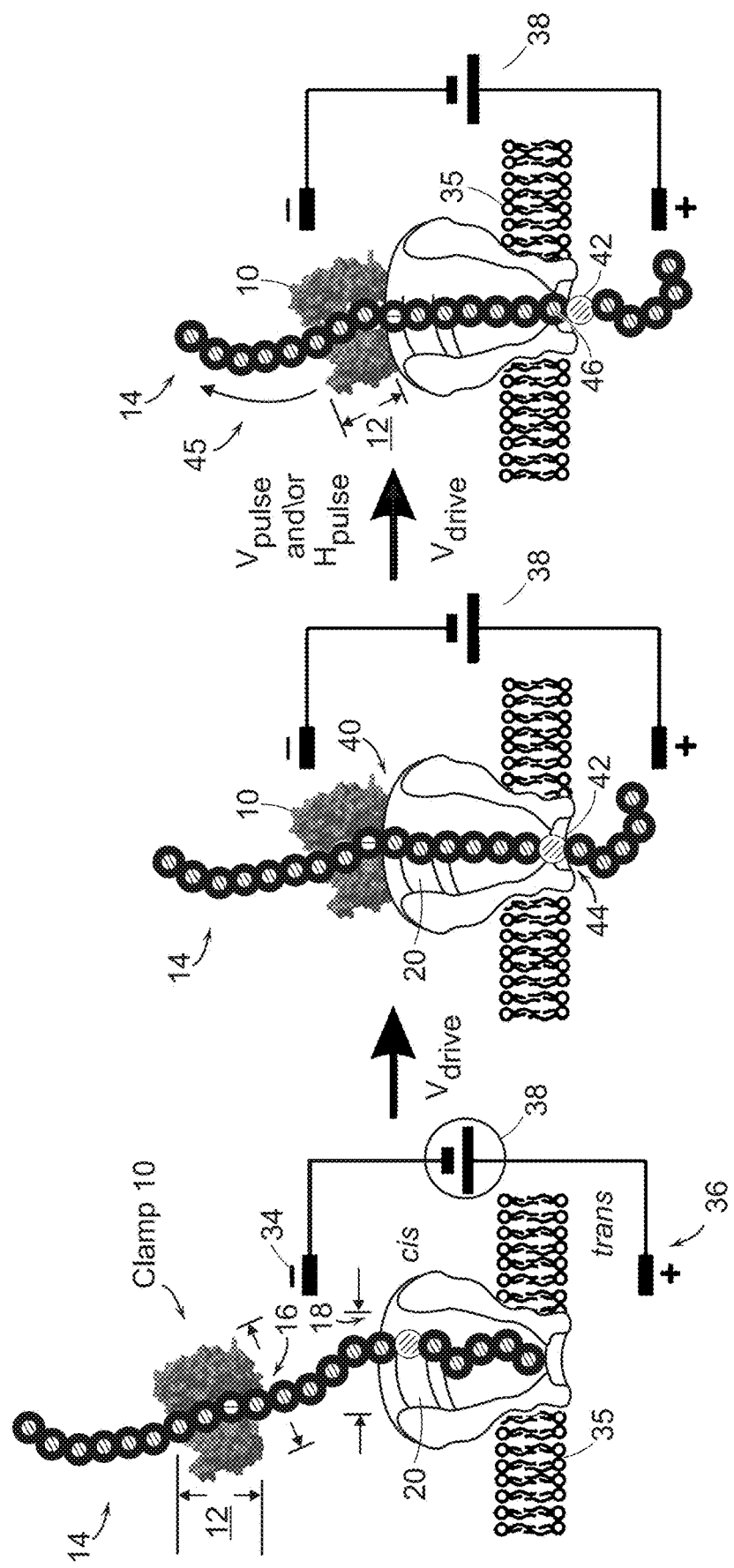

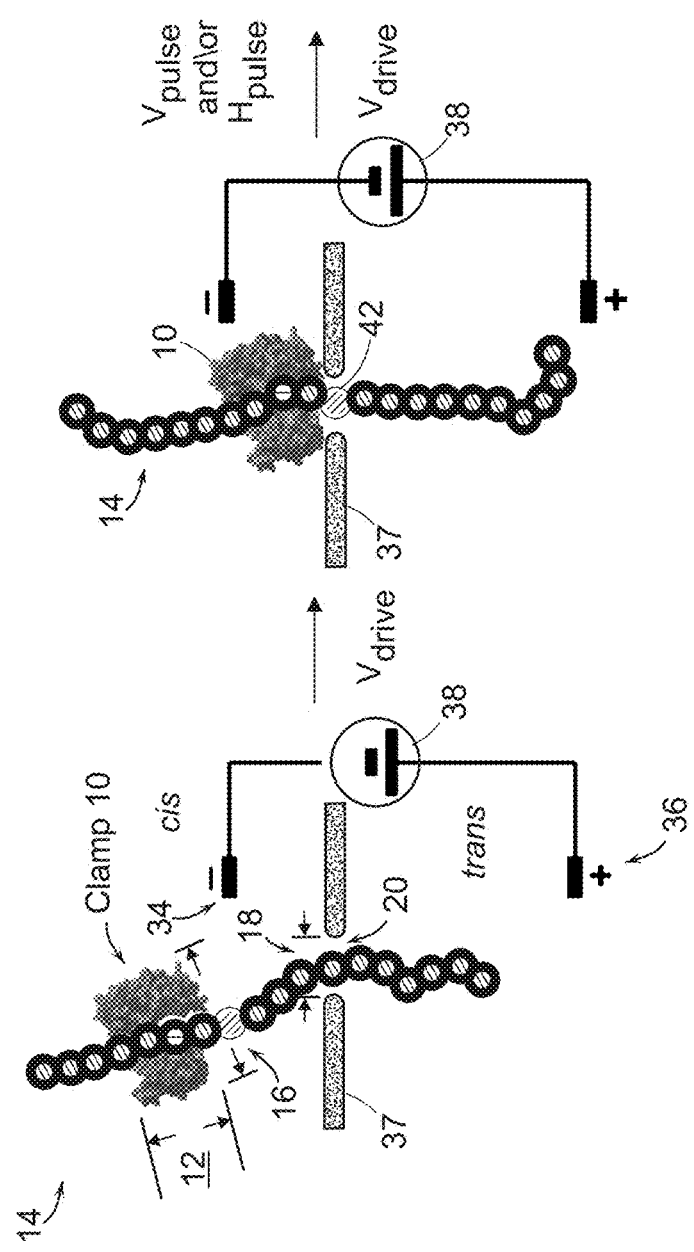

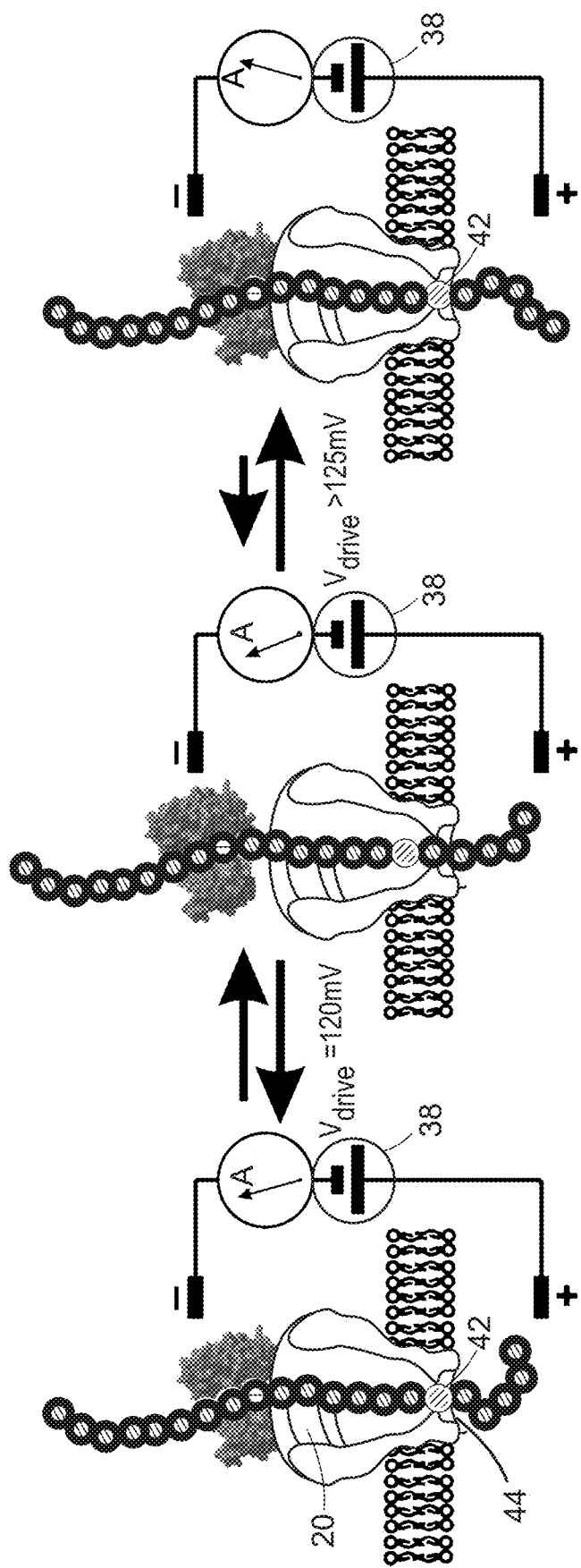

SEQUENCE LISTING

<160> NUMBER OF SEQ ID NOS: 1

<210> SEQ ID NO 1
<211> LENGTH: 27
<212> TYPE: DNA
<213> ORGANISM: Artificial Sequence
<220> FEATURE:
<223> OTHER INFORMATION: nucleobases for clamp advancement

<400> SEQUENCE: 1
tttttgggaa atttttggga aattttc                                         27

DETERMINISTIC STEPPING OF POLYMERS THROUGH A NANOPORE

CROSS-REFERENCE TO RELATED APPLICATION

This application claims the benefit of U.S. Provisional Patent Application No. 62/526,823, filed Jun. 29, 2017, the entirely of which is hereby incorporated by reference.

STATEMENT REGARDING FEDERALLY SPONSORED RESEARCH

This invention was made with Government support under Contract No. HG003703 awarded by the National Institutes of Health. The government has certain rights in the invention.

BACKGROUND

This invention relates to characterization of polymers by translocation of polymers through a nanopore, and more particularly relates to the control of polymer stepping through a nanopore.

A polymer and its subunits can be characterized by measuring changes in the electrical conductance of a nanopore through which the polymer is stepped. Polymer characteristics that have been determined using nanopores include concentration, e.g., the number of molecules in a sample solution, polymer length, number of monomeric units along a polymer length, and the chemical and physical properties of the polymer and its monomer units, including the specific sequence of successive monomer units, as described by Deamer et al., *Nat. Biotechnol.*, 34:518-524, 2016; Manrao et al., *Nat. Biotechnol.*, 30:349-353, 2012; Akeson et al., *Biophys. J.*, 77:3227-3233, 1999; and Cherf et al., *Nat Biotechnol.*, 30:344-348, 2012, all of which are hereby incorporated in their entirety by reference. In one example nanopore-based characterization technique, polymers to be studied are provided in an ionic solution in a cis reservoir that is in fluidic communication with the nanopore. The polymers are translocated through the nanopore from the cis reservoir to a trans reservoir, during which time traversal of the nanopore can be detected and characteristics of the polymer can be determined. Although an electric field produced by the application of a constant voltage bias between cis and trans reservoir electrodes is commonly used to drive polymers through the nanopore, as described by, e.g., Kasianowicz et. al., *Proc. Natl. Acad. Sci.*, 93:13770-13773, 1996, hereby incorporated by reference, other forces can be alternatively employed, including hydrostatic pressure, the forces of optical or magnetic fields, and combinations of two or more of these forces can be used to drive a polymer through a nanopore, as described by, e.g., Lu et al., *Nano Lett.*, 13:3048-3052, 2013; and by Keyser et al., *Nature Physics*, 2:473-477, 2006; both of which are hereby incorporated by reference.

There has been proposed the notion of binding an active enzyme to a polymer to slow or retard the polymer from being freely driven through a nanopore at an undesirably rapid rate, e.g., as taught in U.S. Pat. No. 7,625,706, to Akeson; U.S. Pat. No. 7,238,485, to Akeson; U.S. Pat. No. 7,947,454, to Akeson; U.S. Pat. No. 8,673,556, to Akeson; US 20140051068 to Cherf; US 20140335512 to Moysey; and US 20150031020 to Jayasinghe, the entirety of all of which are hereby incorporated by reference. Such active enzymes, e.g., polymerases or helicases, depend on energy derived from chemical substrates such as adenosine triphosphate (ATP) to walk along the polymer and correspondingly step the polymer through a nanopore. ATP-dependent movement of an active enzyme makes it possible to drive a polymer through a sensing nanopore at a rate that depends on the enzyme's turnover number, i.e., the maximum number of steps the enzyme will take along its polymer substrate per unit time. But as with other concepts derived from studies of bulk liquid phase enzymes, it has been determined that turnover number has little bearing on the behavior of a single molecule's activity where the intervals of time between each active step of a single enzyme molecule varies stochastically around the enzyme's turnover number.

The stochastic interval of time between each successive step of a single molecule at and through a nanopore, e.g., the time between stepping of adjacent monomer units of a polymer through a nanopore, causes major problems because it is during these intervals that the nanopore's electrical conductance is measured and evaluated to characterize the polymer and its polymer subunits in the nanopore. Many of these intervals may be so short as to introduce errors of omission, whereas others may be so long as to be misinterpreted as a succession of identical monomers when in fact no such succession of identical monomer units exists. They also make it impossible to distinguish homopolymer regions of length X (sequences of 4 identical monomers) from those of length X+1, X+2, . . . or X+n).

SUMMARY

In a method provided herein for controlling translocation of a target polymer molecule through a nanopore, a clamp is reversibly bound to a sequential plurality of polymer subunits along the target polymer molecule length. The target polymer molecule includes a sequential plurality of polymer subunits along the target polymer molecule length. The target polymer molecule and reversible bound clamp are disposed in an ionic solution that is in fluidic communication with the nanopore. The nanopore has an aperture diameter that is less than an outer diameter of the clamp.

A constant translocation force is applied across the nanopore to induce travel of the target polymer molecule in the ionic solution into the nanopore, until the clamp on the target polymer molecule abuts the nanopore aperture and stops further travel of the target polymer molecule into the nanopore. Then a control pulse that is at least one of a voltage control pulse across the nanopore and a thermal control pulse at the nanopore is applied. The control pulse has a control pulse duration that steps the clamp along the target polymer molecule by no more than one polymer subunit in a direction opposite that of travel into the nanopore. No fuel is provided to the clamp. The stepping of the clamp causes the target polymer molecule to step further into the nanopore but by no more than one polymer subunit. The control pulse is applied repeatedly to cause a sequential plurality of polymer subunits of the target polymer molecule to translocate through the nanopore.

This translocation control method enables a method for characterizing the target molecule in which a characteristic indication of a polymer subunit is acquired when the polymer subunit is in the nanopore. Here the control pulse is applied repeatedly to cause a sequential plurality of polymer subunits of the target polymer molecule to translocate through the nanopore while acquiring a characteristic indication of each polymer subunit that translocates through the nanopore.

A nanopore system provided herein for characterizing a target polymer molecule includes a first fluidic reservoir and a second fluidic reservoir, the first and second fluidic reservoirs being in fluidic communication with a nanopore that forms a sole fluidic path between the first fluidic reservoir and the second fluidic reservoir. A clamp is provided in the first fluidic reservoir. The clamp abuts the nanopore and is reversibly bound to a sequential plurality of polymer subunits of the target polymer molecule in ionic solution in the first fluidic reservoir. The target polymer molecule includes a sequential plurality of polymer subunits along the length of the target polymer molecule.

A circuit is provided including an electrode in the first reservoir, an electrode in the second reservoir, and a current amplifier for applying a constant voltage bias across the nanopore, between the first reservoir and the second reservoir to induce travel of the target polymer molecule into the nanopore. A voltage pulse generator is connected to the circuit to apply voltage control pulses across the nanopore, between the first reservoir and the second reservoir, to step the clamp along sequential polymer subunits of the target polymer molecule, polymer subunit by polymer subunit, in a direction away from the nanopore, and step the polymer molecule further into the nanopore. The system includes no fuel for the clamp and no source of fuel for the clamp. A computer controller is connected to the circuit to collect an electrical indication of ionic current through nanopore while a sequential plurality of polymer subunits of the target polymer molecule steps through the nanopore.

A further nanopore system provided herein for characterizing a target polymer molecule includes a first fluidic reservoir and a second fluidic reservoir, the first and second fluidic reservoirs being in fluidic communication with a nanopore that forms a sole fluidic path between the first fluidic reservoir and the second fluidic reservoir. A clamp is provided in the first fluidic reservoir. The clamp abuts the nanopore and is reversibly bound to a sequential plurality of polymer subunits of the target polymer molecule in ionic solution in the first fluidic reservoir. The target polymer molecule includes a sequential plurality of polymer subunits along the length of the target polymer molecule.

A circuit is provided including an electrode in the first reservoir, an electrode in the second reservoir, and a current amplifier for applying a constant voltage bias across the nanopore, between the first reservoir and the second reservoir to induce travel of the target polymer molecule into the nanopore. A laser is connected to the computer controller to produce laser pulses and optics are disposed adjacent to the laser and oriented to direct the laser pulses to the nanopore. A material element that is absorptive of energy from the laser pulses is disposed at the nanopore to heat the ionic solution during each laser pulse and in turn to step the clamp along sequential polymer subunits of the target polymer molecule, polymer subunit by polymer subunit, in a direction away from the nanopore, and to step the target polymer molecule further into the nanopore. The system includes no fuel for the clamp and no source of fuel for the clamp. A computer controller is connected to the circuit to collect an electrical indication of ionic current through nanopore while a sequential plurality of polymer subunits of the target polymer molecule steps through the nanopore.

The nanopore systems and methodology provided herein enable the deterministic control of a target polymer molecule's translocation through a nanopore and corresponding superior degree of control in characterization of the target polymer molecule. These and other aspects and embodiments of disclosure are described below and in the accompanying drawings, and in the claims.

BRIEF DESCRIPTION OF THE DRAWINGS

FIGS. 1A, 1B, and 1C are schematic representations of three stages of deterministic stepping of a clamp-articulated polymer molecule through a biological nanopore in a biological membrane;

FIGS. 1D, 1E, and 1F are schematic representations of three stages of deterministic stepping of a clamp-articulated polymer molecule through a nanopore in a solid state membrane;

FIGS. 14A, 14B, and 14C are schematic representations of polymer molecule control by applied bias drive voltage to overcome Brownian motion of the polymer molecule in a nanopore.

DETAILED DESCRIPTION

Figure 2:
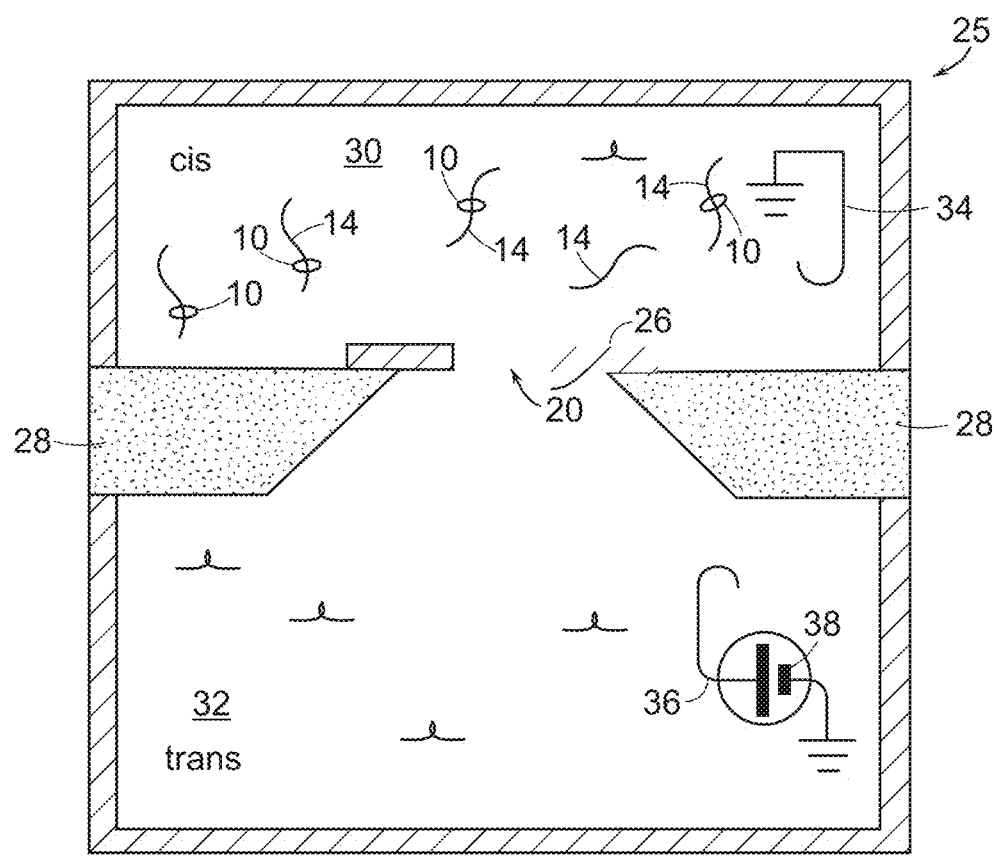
FIG. 2 is a schematic of a nanopore system including clamp-articulated polymer molecules provided in a cis reservoir for deterministic stepping through the nanopore to the trans reservoir.

There are provided herein all of structure, system, and corresponding methodology for deterministic stepping, rather than stochastic stepping, of a target polymer molecule through a nanopore in a nanopore system like that of FIG. 2. In one embodiment, this structure, system and methodology operates to drive linearly connected, sequential, monomer residues of a target polymer molecule through a nanopore with precise deterministic motion, so that the time taken for a repetitive sequence of identical monomer units to traverse through a nanopore identifies the precise number of identical monomers that have translocated through the nanopore. Specifically, when the interval of time between each monomer step through a nanopore is a known constant, k, that is, when stepping is deterministic, as enabled herein, then the total time taken for a repetitive sequence of identical monomer units to traverse through a nanopore, divided by the interval constant, k, identifies the precise number of identical monomers that have traversed through the nanopore.

As shown in FIGS. 1A-1C, herein is provided the structure of a deterministically advancing clamp 10 that reversibly clamps onto, or reversibly binds to, a plurality of monomers 12, e.g., a group of between one and twenty monomers, along a target polymer molecule 14 such as a DNA strand, or other suitable polymer molecule having polymer subunits along the molecule length. The outside diameter 16 of the clamp 10 is greater than the diameter 18 of the aperture, or channel, that extends through the nanopore 20 as shown in FIGS. 1A-1C.

The term "polymer molecule" as used herein is intended to refer to biomolecules, e.g., polynucleotides such as the biopolymer nucleic acid molecules deoxyribonucleic acid (DNA), ribonucleic acid (RNA), synthetic nucleic acids such as peptide nucleic acid (PNA), as well as proteins, sugar polymers, and other biological molecules. The discussion below is therefore not intended to be limiting to a particular implementation. Details related to examples of these molecules, such as polynucleotides, are provided in a range of embodiments for polymer molecular characterization, to illustrate the principles provided herein.

Referring also to the cross-sectional schematic of FIG. 2, this clamp-articulated molecule configuration can be employed in a nanopore system 25 for characterizing a polymer molecule. The nanopore system generally includes a structure 26, such as a membrane, in which is disposed a nanopore 20, either or both of which can be biological or solid state in nature. The membrane or other structure 26 in which is disposed a nanopore can be supported at the edges by, e.g., a support structure 28, if necessary. The structure 26 and support structure 28 are arranged to separate a cis reservoir 30 from a trans reservoir 32 with the nanopore providing the only fluidic path between the two reservoirs. The cis and trans reservoirs include an ionic liquid solution, and the cis reservoir includes target molecules 14 to be translocated through the nanopore 20 to the trans reservoir. Target molecules 14 in the cis reservoir to be translocated through the nanopore each have a reversible clamp 10 disposed at a site along the molecule length, on plurality of polymer subunits, forming a target molecule-clamp complex. A solution of such target molecule-clamp complexes can be produced in the conventional manner as described, e.g., by Moysey, in US 20140335512, hereby incorporated by reference in its entirety. The target molecule-clamp complexes are provided in the cis reservoir for analysis of the target molecules by translocation through the nanopore.

In one embodiment, there is included in the cis reservoir 30 and the trans reservoir 32 electrodes 34, 36, respectively, between which can be applied a constant bias voltage 38. The electric field produced by the application of such a voltage bias between the cis and trans reservoir electrodes 34, 36 can be employed to drive electrically charged molecules in the cis reservoir through the nanopore to the trans reservoir in the conventional manner. But it is to be recognized that other translocation forces can be alternatively employed. Thus, although the stepping control methodology description herein will use the term "voltage bias," or $V_{drive}$, it is to be understood that other forces, including hydrostatic pressure, optical fields, or magnetic fields, and combinations of two or more fields, can also be used to drive a polymer through a nanopore. Henceforth, when the term "constant voltage drive bias," or $V_{drive}$, is used herein, it is to be understood that any one or more of these fields may be substituted. Further details and examples for electrophoretic driving of molecular translocation through a nanopore are provided in "Molecular and Atomic Scale Evaluation of Biopolymers, U.S. Pat. No. 6,627,067, to Branton et. al., issued Sep. 30, 2003, the entirety of which is hereby incorporated by reference.

Now referring to the methodology enabled herein, as shown in FIG. 1A, a target polymer molecule 14 under investigation, including a reversibly bound clamp 10, is shown at a nanopore 20. As shown in FIG. 1B, there is applied a voltage bias, $V_{drive}$, between the cis and trans reservoirs, as in FIG. 2, to provide conditions that are conducive to travel of a target polymer 14 into the nanopore 20. As the target polymer 14 travels into the nanopore, as shown in FIG. 1B, translocation automatically stops when the clamp 10 abuts on a region 40 of the nanopore 20 whose inside diameter 18 is less than the clamp's outer diameter 16, as shown in FIG. 1A. Under this condition, one polymer subunit 42, e.g., one monomer, of the polymer 14, occupies a site within the nanopore, e.g., in a preferred embodiment, occupies the site of a highly-sensitive narrow region 44 of the nanopore 20. As a result, the electrical and volumetric properties of the subunit 42 dominate the nanopore's cis-to-trans conductivity for this condition so long as the subunit 42 remains in the nanopore at a suitable site, e.g., a highly-sensitive region of the nanopore. Sensing, detecting, measuring, or otherwise determining a parameter of the nanopore system related to the nanopore's conductivity therefore provides a characteristic indication of the subunit 42 under this condition.

After a characteristic indication of the subunit 42 is determined, then as shown in FIG. 1C, a control pulse, provided as, e.g., a voltage control pulse, $V_{pulse}$, and\or a thermal control pulse $H_{pulse}$, is provided in addition to the bias drive voltage, $V_{drive}$, across the nanopore. The control pulse steps the clamp 10 along the polymer 14 away from the nanopore 20, in the direction indicated by the arrow 44. The clamp 10 is specifically driven controllably to step one polymer subunit along the polymer and then reversibly bind to a next sequential group 12 of polymer subunits. As a result, the subunit 42 that was in the nanopore is now moved into the solution in the trans reservoir and a next subunit 46 now dominates the nanopore's cis-to-trans conductivity. This process of deterministic stepping of the clamp along the polymer away from the nanopore continued to step the polymer molecule one subunit at a time into and through the nanopore. No energy is applied to the clamp to fuel the stepping of the clamp from one polymer subunit to a next polymer subunit. Specifically, no chemical fuel, and no biochemical fuel is supplied to the clamp. Only the control pulse application causes the clamp to step from one polymer subunit to a next polymer subunit.

FIGS. 1A-1C show a target polymer molecule 14 having a linear sequence of subunits that are represented in the figures as simple circles. This representation is provided solely for clarity of explanation. Target polymer molecules that are loaded into the cis reservoir can be single stranded, as in ssDNA, or can be double stranded, as in dsDNA. In either case, a clamp is disposed at a site on a region of a polymer molecule that is single stranded. Therefore, a double-stranded target polymer molecule is provided with a single-stranded region, to which a clamp can be disposed, in the conventional manner, to enable the siting of a clamp at a point along a single-stranded region of a double-stranded target molecule.

The conditions of FIGS. 1A-1C are shown for an embodiment in which the nanopore 20 is provided as a biological nanopore in a membrane 35 that can be biological or organic, e.g., a lipid bilayer, a tetraether lipid, or a triblock copolymer. For example, the nanopore can be provided as *Mycobacterium smegmatis* porin A (MspA), which is an octameric protein channel, can be provided as the bacterial porin CsgG, which is a ninemer protein channel or can be provided as mutants of these and other channels such as are taught by Moysey in U.S. Pat. No. 9,617,591, the entirety of which is hereby incorporated by reference. The selected biological nanopore is disposed in, e.g., a diphytanoyl phosphatidylcholine membrane (diPhPC), a tetraether lipid, a triblock copolymer, or a solid state structure, such as a solid state membrane composed. Such a solid state membrane can be provided as, e.g., one or more graphene layers, $SiN_x$ or other solid state support through which ions cannot traverse but into which any of the aforementioned biological nanopores can be disposed in a manner that prevents ion flow from cis to trans except through the nanopore's own channel.

The conditions of polymer capture and stepping at a nanopore shown in FIGS. 1A-1C are also shown in FIGS. 1D-1F but for an embodiment of a solid-state nanopore system. As shown in FIGS. 1D-1E, there is applied a constant voltage bias, $V_{drive}$, between the cis and trans reservoirs, as in FIG. 2, to provide conditions that are conducive to capture of a target polymer 14 including a clamp 10, at the site of a nanopore 20. The nanopore 20 here is an aperture, hole, channel, or other opening that is disposed in a solid state membrane 37. The membrane can be formed of any suitable solid state material as described above, e.g., graphene or other atomically-thin material, or as a microelectronic material, such as a nitride, an oxide, or a combination of material layers. The solid state membrane in turn can be supported by a support structure, such as a microelectronic substrate, in the manner of the membrane 26 and support structure 28 of FIG. 2. It is to be recognized that for clarity the system 25 of FIG. 2 is shown with a nanopore 20 that is an aperture in a membrane 26, but any suitable combination of biological, organic, and solid state nanopore and membrane can be employed and is intended for the nanopore system 25 of FIG. 2.

As a target polymer 14 translocates through the nanopore due to the constant bias voltage, translocation automatically stops, as shown in FIG. 1E, when the clamp 10 abuts on the nanopore 20. The nanopore diameter 18 is less than the clamp's outer diameter 16 as shown in FIG. 1D. Under this condition, one subunit 42, e.g., one monomer, of the target polymer 14, occupies the nanopore's most sensitive region. As a result, the electrical and volumetric properties of the subunit 42 dominate the nanopore's cis-to-trans conductivity for this condition so long as the monomer subunit 42 remains in the nanopore. As a result, sensing, detecting, measuring, or otherwise determining a parameter of the nanopore system related to the nanopore's conductivity provides a characteristic indication related to the subunit 42 under this condition.

After a characteristic indication of the subunit 42 is determined, then as shown in FIG. 1F, a control pulse is provided in combination with the bias drive voltage, $V_{drive}$, as, e.g., a voltage control pulse, $V_{pulse}$, and\or a thermal control pulse $H_{pulse}$, to step the clamp 10 along the target polymer 14 away from the nanopore 20, in the direction indicated by the arrow 44. The clamp 10 is specifically driven to step along the polymer by one monomer subunit and then to bind to a next group of polymer subunits. As a result, the subunit 12 in the nanopore is moved into the trans reservoir and a next subunit 46 now dominates the nanopore's cis-to-trans conductivity. This process of deterministic stepping of the clamp along the target polymer is continued to step the polymer molecule one subunit at a time into and through the nanopore.

Figure 3:
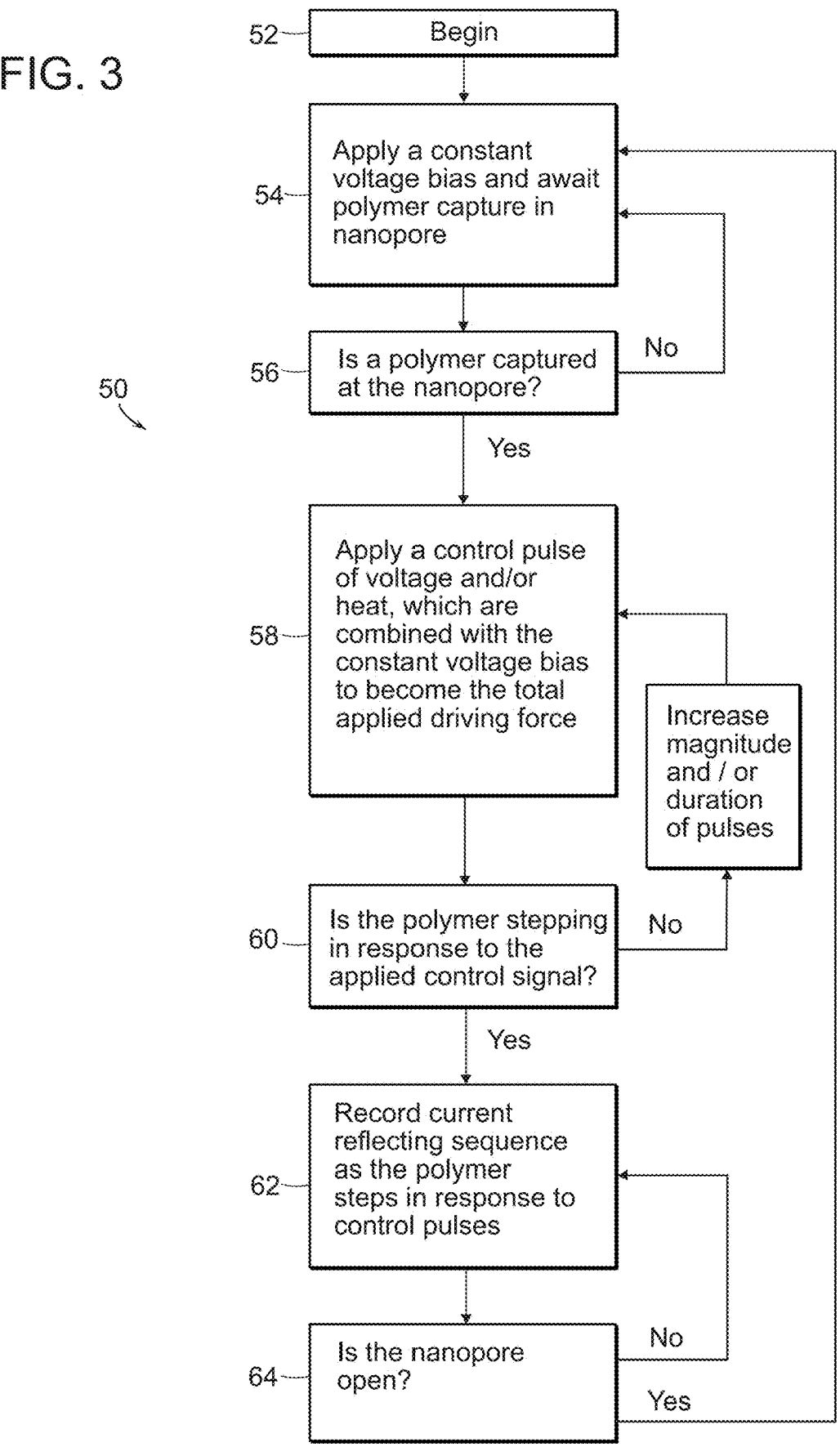
FIG. 3 is a flow chart of methodology steps for carrying out deterministic stepping of a clamp-articulated polymer molecule through a nanopore.
Figure 4A:
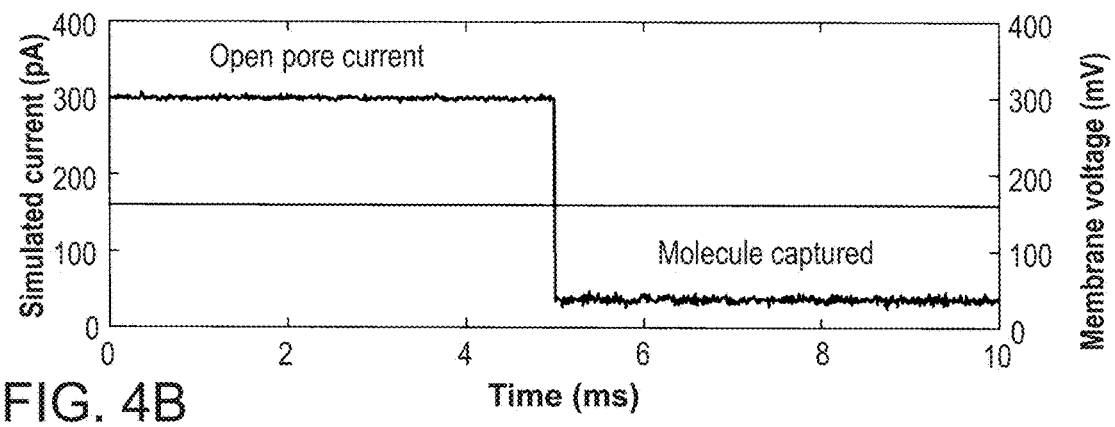
FIGS. 4A, 4B, 4C, and 4D are plots of nanopore current to be measured or control pulse voltage to be applied in carrying out the methodology steps of the flow chart of FIG. 3.

FIG. 3 is a flow chart of method steps for implementing the conditions shown in FIGS. 1A-C and FIGS. 1D-F, and FIGS. 4A-4D are plots of measured electrical signals that are indicative of the conditions for each of the method steps. In the methodology 50, after assembling the nanopore system to begin 52 the method with target polymer molecules articulated with clamps disposed in the cis reservoir, then in a first step 54, a constant bias driving voltage, $V_{drive}$, is applied between the cis and trans reservoirs. In a next step 56, it is determined 56 if a target polymer has been captured at the nanopore. FIG. 4A is a plot of current as a function of time measured for a nanopore, showing that when a target polymer is captured at a nanopore, the current measured through the nanopore dramatically decreases from an open pore current level to a lower level indicative of polymer molecule capture in the nanopore. If it is determined that a polymer has not been captured at the nanopore, then the constant voltage bias is maintained and determinations are continued until it is verified that a polymer has been captured at the nanopore.

Figure 4B:
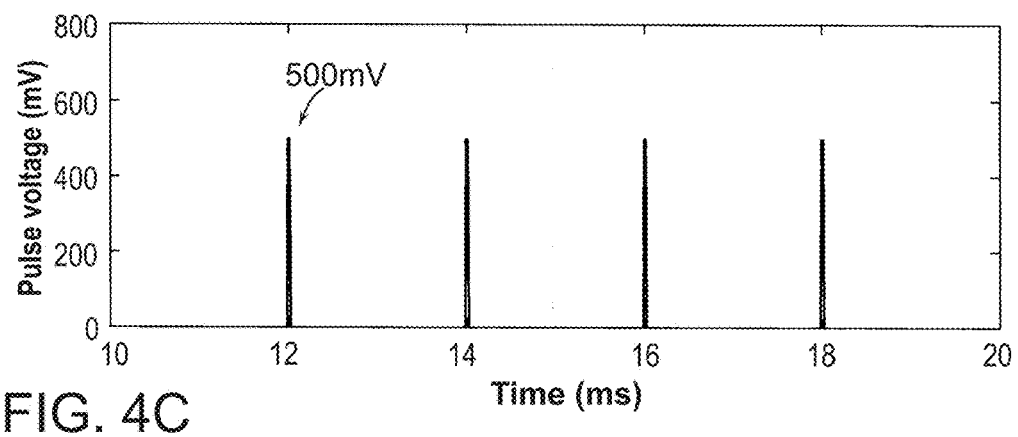
Figure 4C:
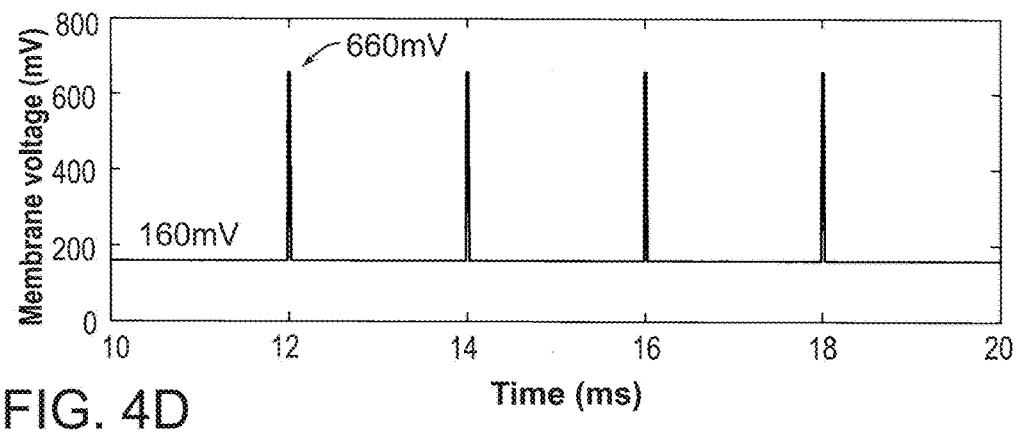

In a next step 58, control pulses, such as voltage and/or heat control pulses, are applied in addition to the bias voltage, between the cis and trans reservoirs. In one embodiment, here for a voltage control pulse, as shown in the plot of FIG. 4B, voltage pulses are applied across the nanopore. Then as shown in the plot of FIG. 4C, the total voltage across a nanopore includes the addition of the constant bias voltage and the pulse voltages. The timing and duration of each pulse can be controlled either manually or by an automated system that can provide continuously repeating pulsing. The polarity of the bias voltage and pulse voltages are the same with respect to the nanopore, so that that sum of the bias voltage and the voltage pulses is additive, and is oriented in a direction that drives the polymer through the nanopore, for a given polymer charge.

Figure 4D:
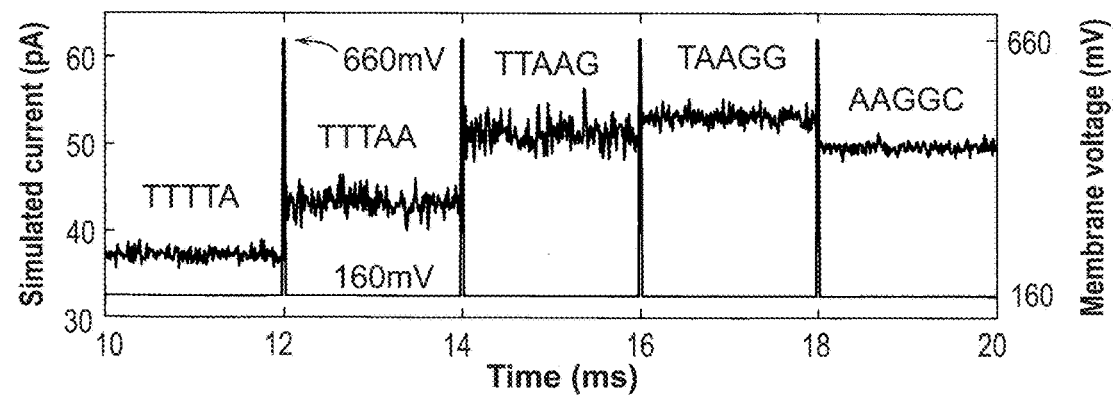

In a next step 60 it is determined if the target polymer is stepping through the nanopore in response to the applied control pulses. The plot of FIG. 4D provides an example showing that with a current measurement it can be determined that the target polymer takes a single step of one polymer subunit in response to a single voltage pulse. If it is determined that the polymer is not taking a single step in response to a single voltage pulse, or in response to a single heat pulse, then the magnitude and/or duration of the pulses are increased. When it is indicated that the polymer is stepping through the nanopore by one polymer subunit in response to one applied pulse, then in a next step there is acquired some representative indication reflective of the characteristics of the polymer subunit at the nanopore sensing site. For example, as shown in FIG. 3, in this step 62 measured current through the nanopore can be acquired and if desired, recorded, to reflect characteristics of polymer subunits as the polymer steps through the nanopore in response to the control pulses.

In a final step 64, it is determined if the nanopore has become open, e.g., by determining if the nanopore current has returned to the open pore current. If not, then the step 62 of recording the polymer sequence is continued. If the nanopore is determined to be open, then step 54 is again conducted, with only the constant bias voltage applied across the nanopore while awaiting capture of a target polymer molecule at the nanopore.

In the methodology 50, the step of measuring nanopore current can be conducted to acquire a range of different characteristic indications of a polymer subunit in the nanopore. In general, the acquisition of characteristic indications of a polymer subunit can be conducted as, e.g., detection of the existence of a polymer subunit in the nanopore; counting of a polymer subunit in a sequential plurality of subunits; identifying a number of identical subunits in a sequential plurality of subunits; identifying a polymer subunit; determining a chemical aspect of a subunit, or other characteristic indication of a subunit. The sequential sequence of subunits along an entire polymer molecule can be characterized in this manner, providing number and identity information for the entire polymer molecule sequence.

Figure 5:
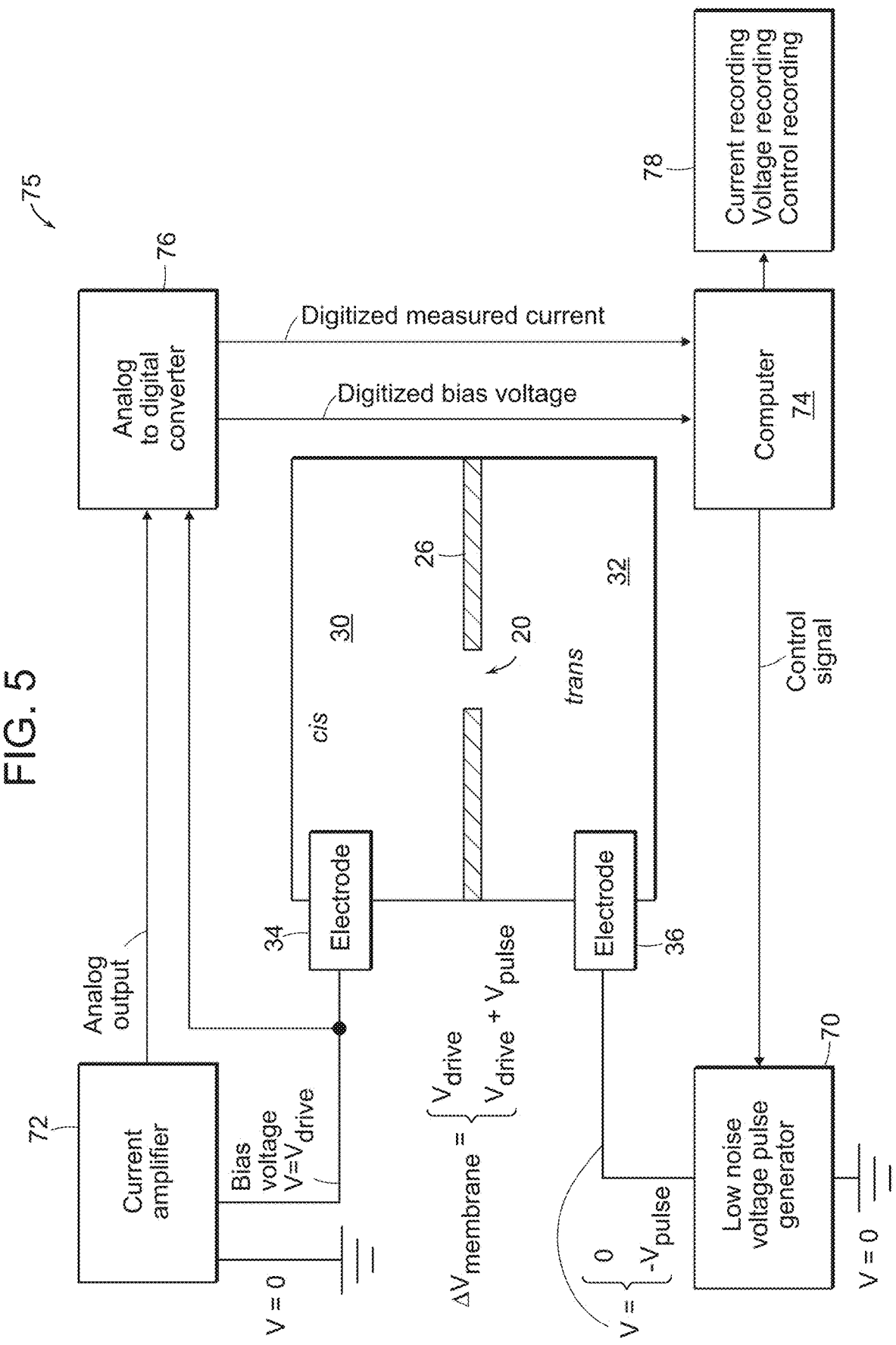
FIG. 5 is a schematic of a nanopore system and associated electronics for implementing voltage control pulse application in deterministic stepping of a clamp-articulated polymer through a nanopore.

This controlled stepping method can be implemented with any suitable system of electronic control. FIG. 5 is a schematic diagram of an embodiment in which a system 75 is arranged for implementing the methodology of FIG. 3 with control pulses that are voltage control pulses. In the system 75, electrodes 34, 36, are provided in the cis and trans reservoirs, and are connected to a low-noise voltage pulse generator 70 and a current amplifier 72. The current amplifier 72 is controlled to apply the constant bias voltage, $V_{drive}$, between the cis and trans reservoirs. The pulse generator 70, when triggered by a control signal from a controlling computer 74, produces a voltage control pulse, $V_{pulse}$, that is added to the bias voltage, $V_{drive}$, to be applied between the electrodes 34, 36. The current amplifier 72 provides an analog output measurement of nanopore current, which is digitized by an analog to digital converter 76 and provided to the computer 74 for recording. The circuit formed by the cis and trans reservoirs, the nanopore, the current amplifier, A/D converter, pulse generator, and computer, enables a measurement of electrical current in the circuit that is indicative of the ionic current through the nanopore.

The system can be temperature-controlled as-needed and in any suitable fashion, e.g., with a thermoelectric heater/cooler. No element of the system provides energy to the clamp to fuel stepping of a clamp along a polymer molecule and no source of energy is included in the system. As explained above, only the voltage control pulses cause the clamp to step along a polymer molecule.

Figure 7:
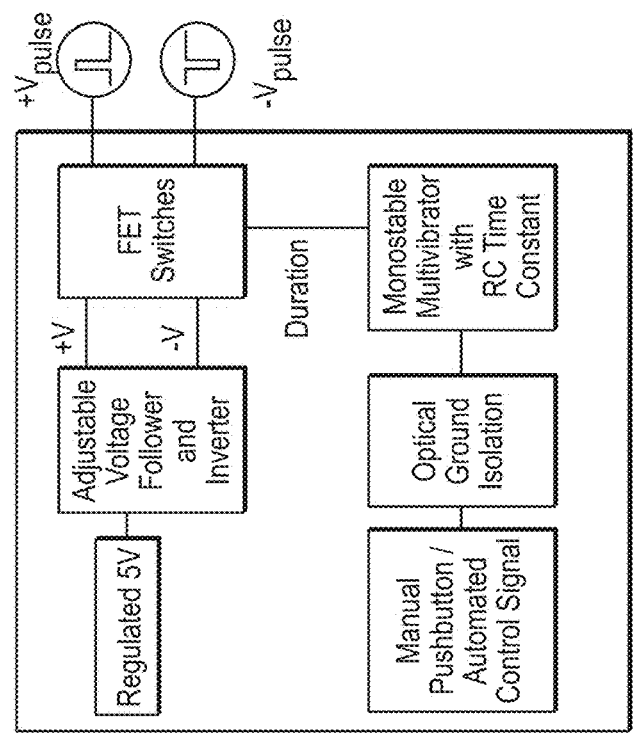
FIG. 7 is a schematic block diagram of the low-noise voltage pulse generator of the system of FIG. 5.
Figure 6:
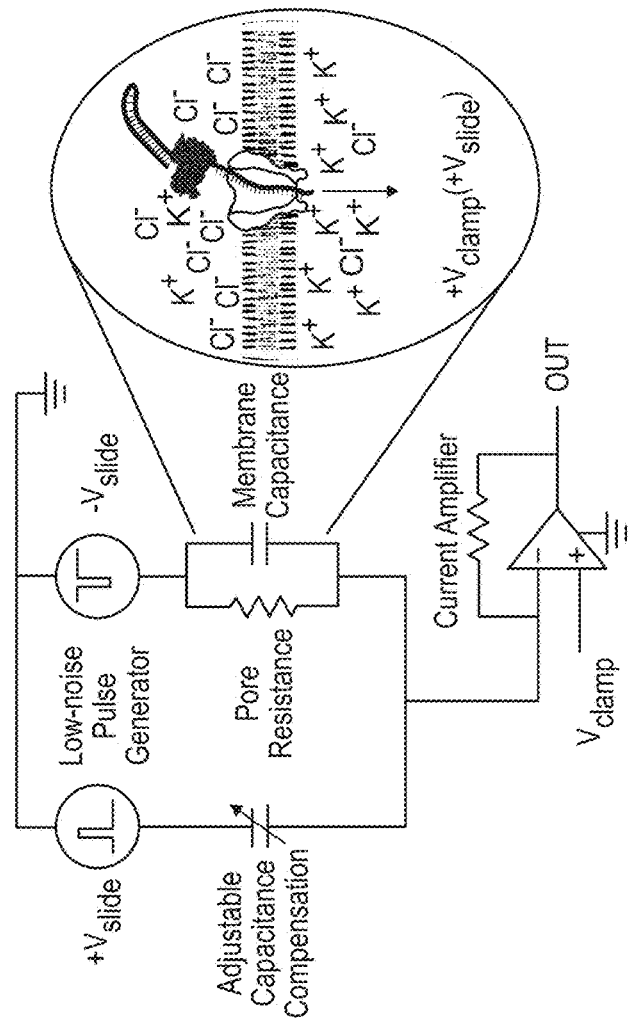
FIG. 6 is an electrical circuit model of the nanopore system including control pulse voltage application electronics.

This system 75 can be electrically modelled with an electrical circuit model 80 as shown in FIG. 6. A nanopore in a membrane gives rise to pore resistance and membrane capacitance. FIG. 7 is a schematic diagram of one embodiment for the low-noise voltage pulse generator 70 of FIG. 5. The low-noise pulse generator includes control elements that determine the duration of time between control pulses as well as the duration and amplitude of the voltage control pulses. This embodiment can be particularly preferred to enable precise production of voltage control pulses. Specifically, in preferred embodiments, there is generated capacitance compensation, $+V_{pulse}$ and $-V_{pulse}$, as shown in FIG. 7, provided by a voltage follower-inverter, to reduce capacitance-caused 'overshoots' whose durations can make it impossible to measure the actual current through the nanopore when the intervals of time between voltage pulses are set to be a minimal interval, e.g., for maximizing nanopore data output.

Figure 8:
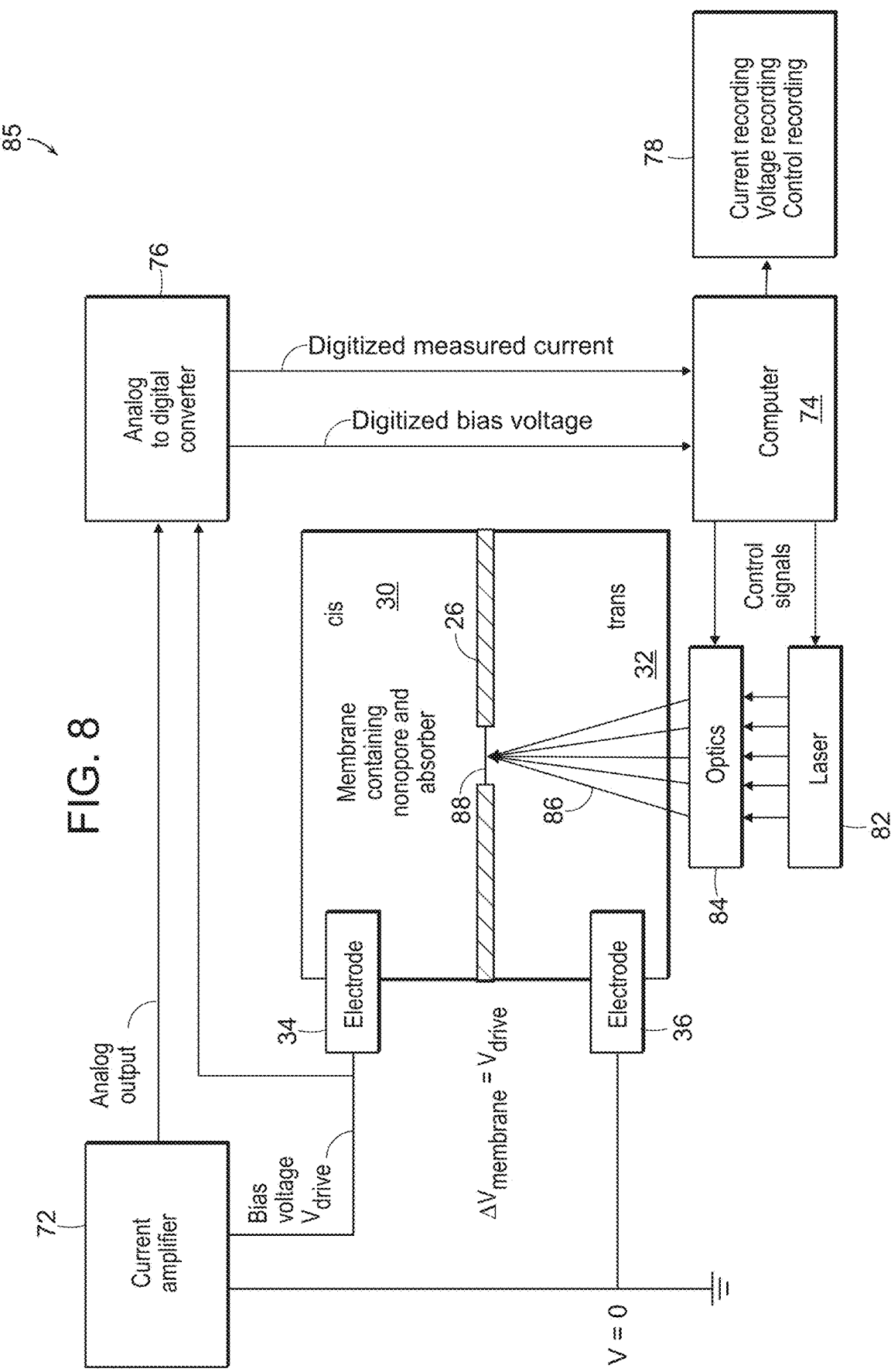
FIG. 8 is a schematic of a nanopore system and associate componentry for implementing heat control pulse application in deterministic stepping of a clamp-articulated polymer through a nanopore.

FIG. 8 is a schematic diagram of an embodiment in which a nanopore system 85 is arranged for implementing the methodology of FIG. 3 with control pulses that are heat control pulses. In the system 85, electrodes 31, 36, are provided in the cis and trans reservoirs, and are connected to a current amplifier 72. A current amplifier 72 provides a constant bias voltage, $V_{drive}$, between the cis and trans reservoirs. Control pulses of heat are produced by control from the computer 74, providing triggering pulse control signals to a laser 82 and optics 84 that are arranged for directing pulses of laser energy 86 to the site of a nanopore in a membrane at which is disposed a material that is absorptive of the laser energy 86. The absorbance of the laser energy by the absorptive material causes a pulse in temperature increase near the nanopore, as explained below. The current amplifier 72 provides an analog output measurement of nanopore current, which is digitized by an analog to digital converter 70 and provided to the computer 74 for recording in the manner of the voltage pulse control system of FIG. 5. As with that system, the system 85 here can be temperature-controlled as-needed and in any suitable fashion, e.g., with a thermoelectric heater/cooler.

Figure 9A:
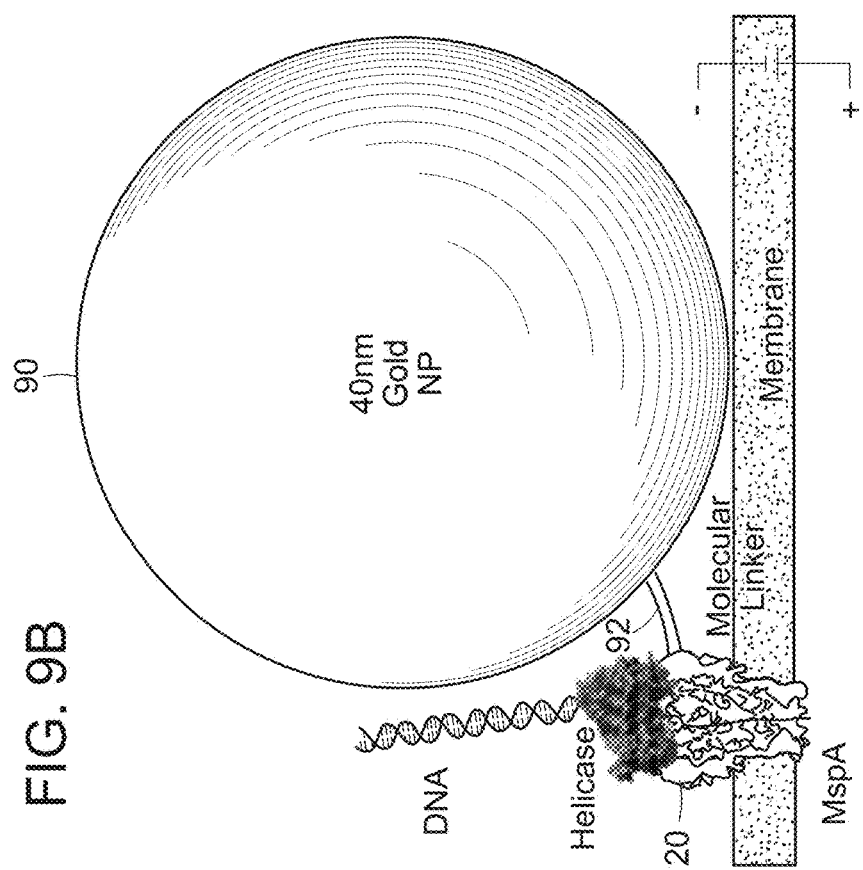
FIGS. 9A and 9B are schematic representations of a gold nanoparticle (NP) linked to a clamp and linked to a nanopore, respectively, for providing the absorptive material in the nanopore system of FIG. 8.
Figure 9B:
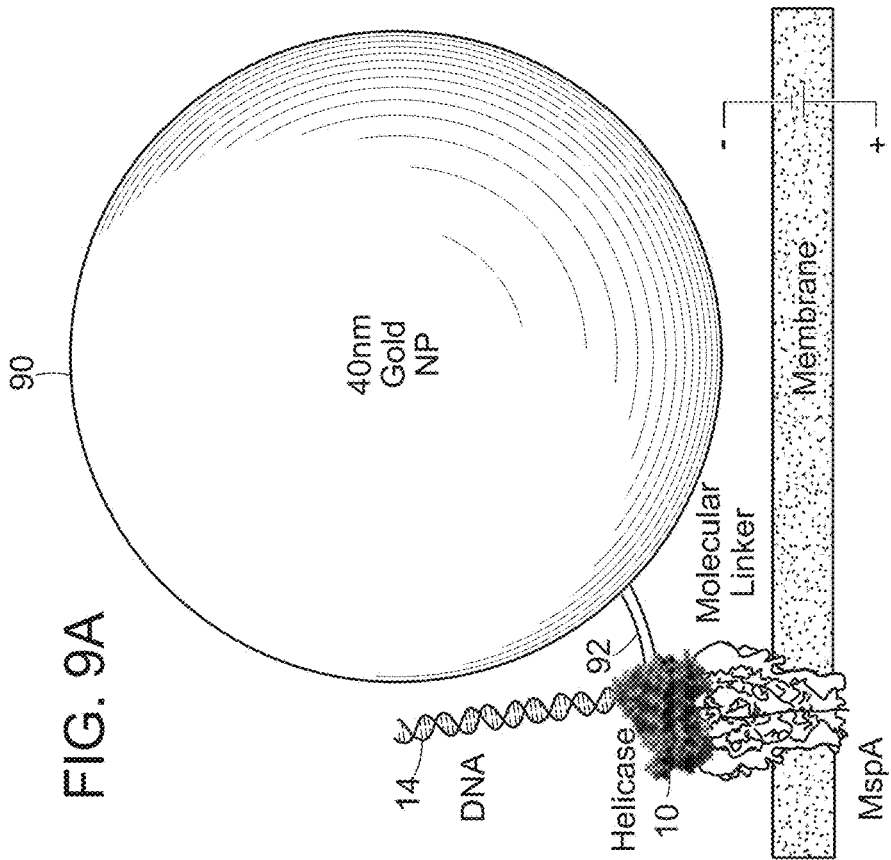

FIGS. 9A-9B illustrate embodiments for providing an absorptive material at the site of the nanopore in the system 85 of FIG. 8. In a first embodiment, shown in FIG. 9A, there is provided an absorber particle 90, such as a gold, silver, or other suitable nanoparticle (NP), that is attached to the clamp 10 by way of a molecular linker 92. In a further embodiment, shown in FIG. 9B, an absorber particle 90, such as a gold NP, is attached to the nanopore 20 by means of a molecular linker 92.

In either of these two embodiments, illumination of the particle, preferably a gold NP, with laser light whose wavelength takes advantage of plasmon resonance effects on gold particles is particularly effective at rapid local heating of the solution in the vicinity of the nanopore. Because the highly confined surface plasmon resonance effect in gold nanoparticles enhances the absorption of light by the particle, visible laser light incident on the nanoparticles causes a rapid and large increase of the particle temperature and adjacent solution temperature. This temperature increase can be estimated from the change in the nanopore's ionic conductance. For example, a 532 nm-wavelength laser operating at a beam energy 300 mW can easily increase the temperature of a gold nanoscale-diameter particle and the areas immediately-surrounding the NP from room temperature by between about 20 C and about 50 C in only nanoseconds. Because the volume that is heated can be as small as a few yoctoliters, this small volume can rapidly return to the temperature of the surrounding solution volume because its thermal energy is rapidly dissipated into the surrounding solution whose volume will usually be at least 16 orders of magnitude larger.

In a further embodiment, the control system 75 of FIG. 5 is combined with the control system 85 of FIG. 8 to enable a combination of voltage and thermal control pulses. With an absorber, such as a gold NP in place at the nanopore, both voltage and heat pulsing are employed for deterministic monomer movement in the manner described above. The timing and duration of each voltage and thermal pulse can be controlled separately either manually or by an automated system, with coordination of thermal pulsing control with voltage pulsing control.

Now turning to particulars of the clamp 10 to be employed with the nanopore system, the clamp shown in FIGS. 1A-1C can take on any suitable configuration and arrangement that enables the clamp to reversibly clamp to, or reversibly bind to, a plurality of polymer subunits of a target polymer to be translocated through a nanopore or other subunits of a molecule in general. Although the clamp can be a molecule that in other systems functions as an enzyme or biochemical fuel-dependent motor, herein the term "clamp" is intended to refer to any biological molecule or non-biological assembly, i.e., solid state assembly, that reversibly binds to a polymer and that can be deterministically driven to step or move in single consecutive monomer steps through the length of the polymer by the application of voltage control pulses, $V_{pulse}$, and\or thermal control pulses, $H_{pulses}$, instead of with biochemical fuel-dependent action. No chemical or other fuel is provided for the clamp to make steps along the sequence of polymer subunits of a target polymer molecule.

In one embodiment, the clamp is a helicase, such as a T4 Phage helicase enzyme. In other embodiments, other enzymes, including mutants of the T4 Phage helicase enzyme, and other proteins and biochemical or inorganic chemical complexes which bind to nucleic acid polymers, can also be employed as the clamp.

With such a clamp and the control systems described above, the polymer stepping methodology provided herein avoids stochastic movement of an enzymatically-active molecule by using a clamp whose motion does not require ATP or the input of chemical or biochemical fuel, and instead is deterministically driven by voltage control pulses, $V_{pulse}$, and\or thermal control pulses, $H_{pulse}$, superimposed on a constant voltage bias, $V_{drive}$. As a result, there is herein provided a method in which a linear sequence of target polymer monomers is translocated through a nanopore with precisely timed stepping motion. Two features particularly enable this methodology.

First, unlike biochemically-fueled arrangements for enzymes such as helicases and polymerases, which have been used to control the stochastic motion of a polymer through a nanopore, the methodology herein requires that the deterministically driven clamp not use a source of chemical energy to cause the clamp to move along the monomer subunits of a target polymer. Instead, herein a voltage control pulse, $V_{pulse}$, and\or a thermal control pulse, $H_{pulse}$, is controllably applied with a constant driving voltage bias, $V_{drive}$, to very briefly release, or loosen, the polymer-bound clamp such that the clamp slides one, and only one, monomer step along the polymer as the polymer is driven to step through the nanopore by one monomer as shown in FIG. 1C. Therefore, except when the clamp moves relative to the target polymer, as in FIG. 1C, the bound clamp prevents, or stalls, the target polymer from being driven through the nanopore by the driving force that would, absent the clamp, rapidly drive the full length of the polymer through the nanopore. In effect, the clamp serves the function of the pawl on a clock ratchet wheel, and the bias voltage, $V_{drive}$, serves as the spring or motor that propels the ratchet wheel.

Secondly, the voltage control pulses and/or heat control pulses, which are preferably of nanoseconds to microseconds in duration, e.g., one millisecond or less, step the target polymer strand through the nanopore by causing the clamping component to slide one monomer unit per pulse along the polymer. Because the constant voltage bias, $V_{pulse}$, is continuously acting to electrophorese, or drive, the polymer through the nanopore through which the bound clamp cannot move, given its greater diameter, the polymer steps deterministically through the nanopore one monomer unit at a time as the clamping component reversibly, but deterministically, slides and then reversible re-clamps to the polymer at another plurality of monomer units.

In preferred embodiments, the duration of a single voltage control pulse, $V_{pulse}$, and\or thermal control pulse, $H_{pulse}$, is adjusted to be no longer than that required to momentarily release the clamp from the polymer, whereupon the constant bias voltage, $V_{drive}$, drives the polymer through the nanopore as the clamp slides one monomer step along the polymer, in the direction shown by the upward-pointing arrow in FIG. 1C, to bind to the next successive monomer unit or group of monomer units. This brings the next successive monomer unit of the polymer to occupy the nanopore and preferably to occupy narrowest region of the nanopore, which is the most sensitive, such that the nanopore's conductivity is now dominated by the electrical and volumetric properties of this next successive monomer or group of monomers. A series of these voltage and\or thermal control pulses therefore functions in the manner of the pawl-release mechanism of a clock system. A succession of voltage and\or thermal control pulses thereby steps the full length of a target polymer to be driven through the nanopore.

Not that even if the clamp is implemented as a molecular clamp enzyme that could potentially utilize ATP or another biochemical fuel to turnover and step along the polymer, no ATP or source of chemical energy is to be provided in the methodology herein and the clamp is made to slide along its polymer substrate only by voltage and thermal control pulsing, with $V_{pulse}$ and\or $H_{pulse}$. Since the clamp is driven along the polymer by a precisely timed voltage control pulse, $V_{pulse}$ and\or thermal control pulse, $H_{pulse}$, the stepwise movement of the polymer through the nanopore is deterministic.

Both deoxy-nucleotide triphosphate (dNTP)-driven polymerases and ATP-dependent helicases have been used to stochastically step DNA through a nanopore for sequencing. It is known that the stepping rate of both of these and other chemically-driven enzymes can be accelerated, decelerated, or even brought to a stall by mechanical forces. It is also known that in the presence of ATP or dNTPs, nucleic acid-stepping enzymes such as helicases and polymerases step along a polymer substrate monomer by monomer without skipping or jumping several monomers even when mechanically accelerated or decelerated. For example, if the clamp 10 as-shown in FIGS. 1A-C is a helicase that in the presence of ATP normally steps along a polymer substrate in the direction shown by the upward arrow in FIG. 1C, this stepping becomes more rapid—but still steps monomer by monomer without skipping—as the voltage bias that drives the polymer from a cis reservoir to a trans reservoir through a nanopore is increased, as taught by Moysey in U.S. Pat. No. 9,617,591, the entirety of which is hereby incorporated by reference.

Figure 10:
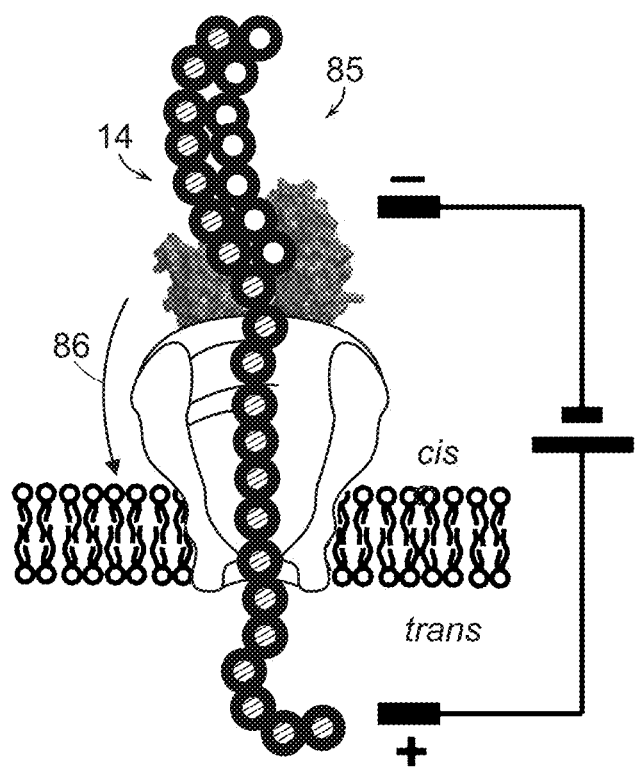
FIG. 10 is a schematic representation of polymerase synthesis.

Conversely, referring to FIG. 10, if the clamp is a processive polymerase 85, then the stepping of the polymerase in the presence of dNTPs along a polymer in the direction of the arrow 86 tends to step the polymer out of the nanopore more slowly—but still steps the polymer monomer by monomer without skipping—as the electrophoretic force of the voltage bias that drives the polymer cis to trans becomes greater, as described by Lieberman et al., *J. Am. Chem. Soc.*, 132:17961-17972, 2010, the entirety of which is hereby incorporated by reference. Finally, the fact that the F1-ATPase, which normally consumes ATP to step counter-clockwise, synthesizes ATP when driven clockwise by a purely mechanical force clearly demonstrates that a mechanical force working at one particular point on a protein machine can drive a chemical reaction at a catalytic site. These examples show that appropriately applied mechanical forces do not rupture or destroy the normal conformational changes of an enzyme. Furthermore, these examples provide unequivocal evidence that purely mechanical forces can retard, facilitate, or, even drive what are normally chemical-energy driven conformational changes.

The fact that a mechanical force can, in the presence of ATP, facilitate, retard, or substitute for the conformational modification of an enzyme that causes it to step raises the following question, addressed by the structure provided herein. Absent any ATP, i.e., absent any fuel, can a purely mechanical force alone cause a polymer-stepping enzyme to undergo the conformational modifications that cause it to slide along a polymer with the same monomer-by-monomer precision that characterizes ATP-dependent steps? When using the chemical energy derived from hydrolysis of ATP, an enzyme such as a helicase undergoes a conformational change that advances the helicase precisely one, and only one, nucleobase per step along a polymer. If a mechanical force acting alone were to simply push an enzyme clamp to randomly slide over an indeterminate number of nucleobases at each step, then a sequence of nucleobases sensed by the nanopore would fail to report the actual sequence of nucleobases in the polymer because identification of each successive nucleobase by the nanopore occurs in the time interval between each successive step.

Figure 11:
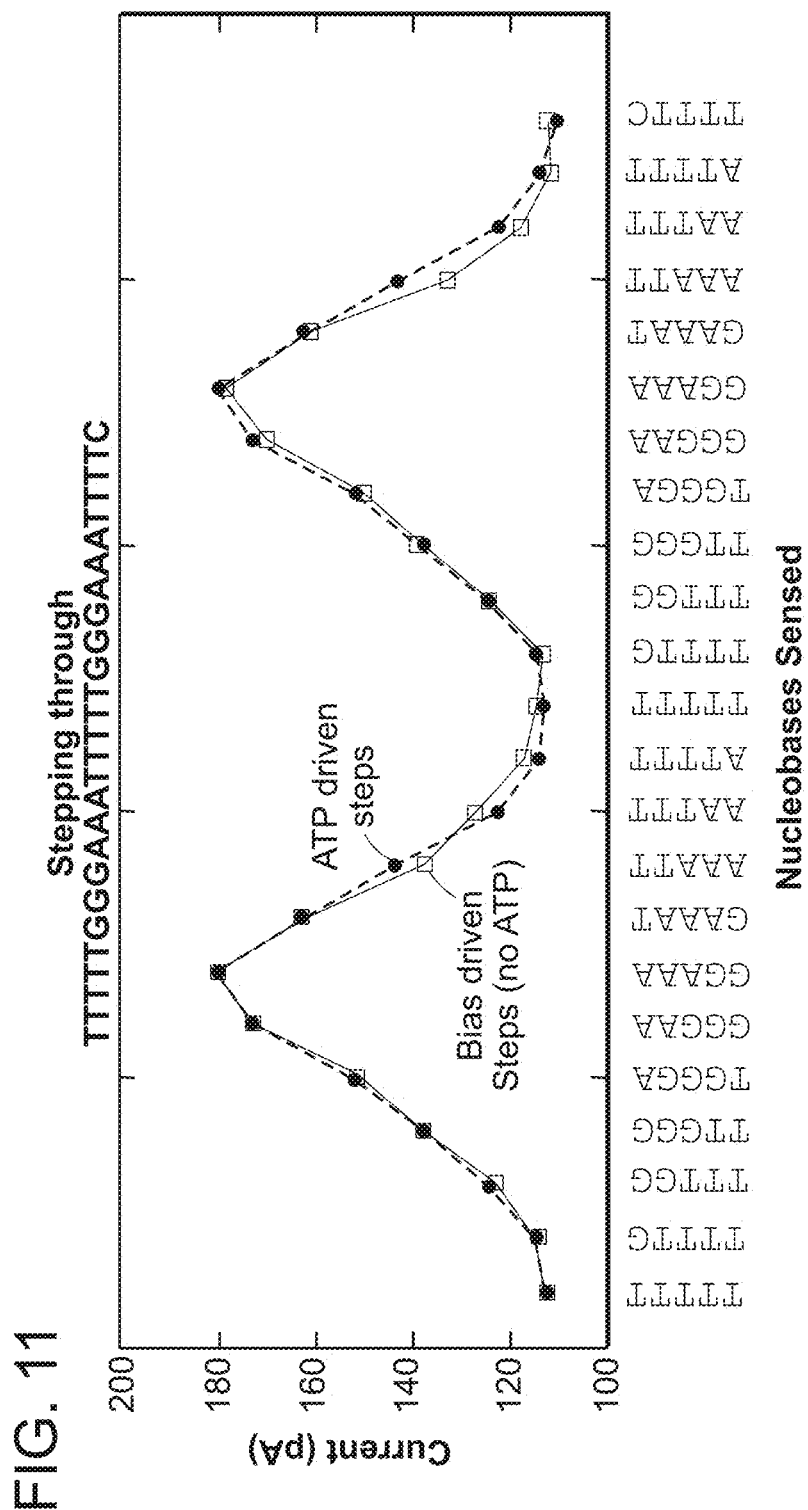
FIG. 11 is a plot of measured nanopore current as a function of about 5 nucleobases adjacent to a sensed monomer for the conditions of ATP-driven polymer stepping and voltage bias-driven polymer stepping with no ATP, both with a T4 helicase polymer clamp, with the sequence of DNA shown above the plot (SEQ ID NO: 1) read as a series of overlapping 5-mers shown below the horizontal axis.

Referring now to the plot of FIG. 11, it is discovered by the inventors herein that an applied force can push an enzyme clamp to advance precisely one, and only one, nucleobase per step in the manner enabled by ATP, but completely in the absence of ATP, i.e., without any fuel provided to the clamp. The plot of FIG. 11 shows nanopore current blockage due to about 5 nucleobases that are immediately adjacent to a monomer that occupies a nanopore's narrowest regions at each step of a DNA strand. The sequence of the DNA is read as a series of overlapping 5-mers, as shown for the horizontal axis.

As shown in the plot of FIG. 11, the current through a nanopore at each step of a voltage bias-driven DNA strand (circles) is the same (within the error limits for such current readings) as the current reading at each step of an ATP-driven strand (squares), for an applied voltage bias, of $V_{drive}=160$ mV. This shows that a mechanically-forced movement can advance a polymer, such as a DNA strand, forward through a nanopore by one nucleotide just as can an ATP-fueled force, and can do so without the use of ATP. Thus, the voltage-forced movement can faithfully move the target polymer molecule through the nanopore and therefore enable a sequence of current levels that are the same as when the polymer movement through the nanopore is controlled by, e.g., an ATP-fueled helicase enzyme. This clearly shows that a purely mechanical force of sufficient magnitude causes what is normally an ATP-dependent enzyme to serve as a clamp that can in the absence of ATP be driven by voltage and/or thermal control to move along the length of a DNA strand with the same monomer-by-monomer stepping precision as does an ATP-dependent DNA motor enzyme.

While plot of FIG. 11 illustrates the normal 5' to 3' stepping of an ATP-driven T4 helicase as well as mechanically-driven 5' to 3' T4-helicase serving as a clamp in the absence of ATP, the T4-helicase could also have been mechanically driven in reverse along the DNA strand, that is from 3' to 5'. Indeed, considering what has been observed by Milkidjanian et al., *Nat. Rev. Microbiol.*, 5:892-899, 2007, hereby incorporated by reference in its entirety, with the F1-ATPase, which instead of hydrolyzing ATP can synthesize ATP when driven in reverse by a mechanical force, as described by Ito et al., *Nature*. 427:465-468, 2004, hereby incorporated by reference in its entirety, it is understood that ATP can be generated, rather than consumed, by driving an ATP-dependent, nucleic acid-stepping motor enzyme in reverse of its normal 5'-to-3' or 3'-to-5' movement direction along DNA. As a result, in a further embodiment provided herein, the bias driving voltage and voltage control pulses and/or thermal control pulses can be employed to move a clamp in either of the two possible directions along a polymer molecule length.

Figure 12:
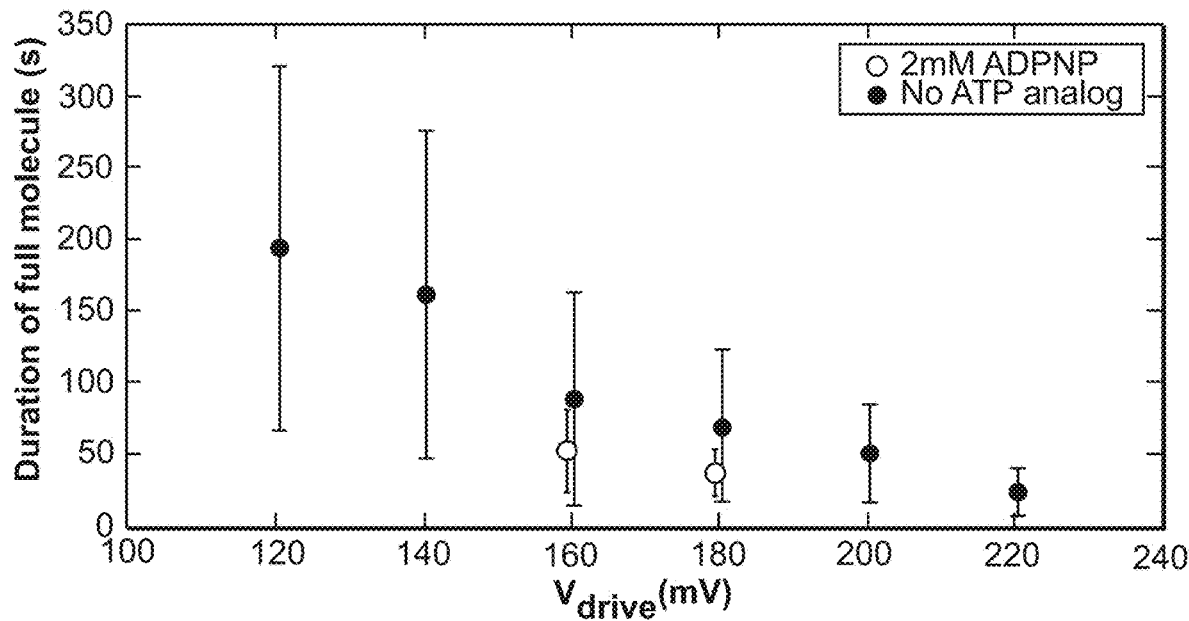
FIG. 12 is a plot of the median measured duration for traversal of a full-length polymer using a T4 phase helicase as the polymer clamp, for a 2 mM ADPNP and for no ATP analog, with the vertical capped lines indicating the duration time range for several identical polymers to completely traverse through the nanopore.
Figure 13:
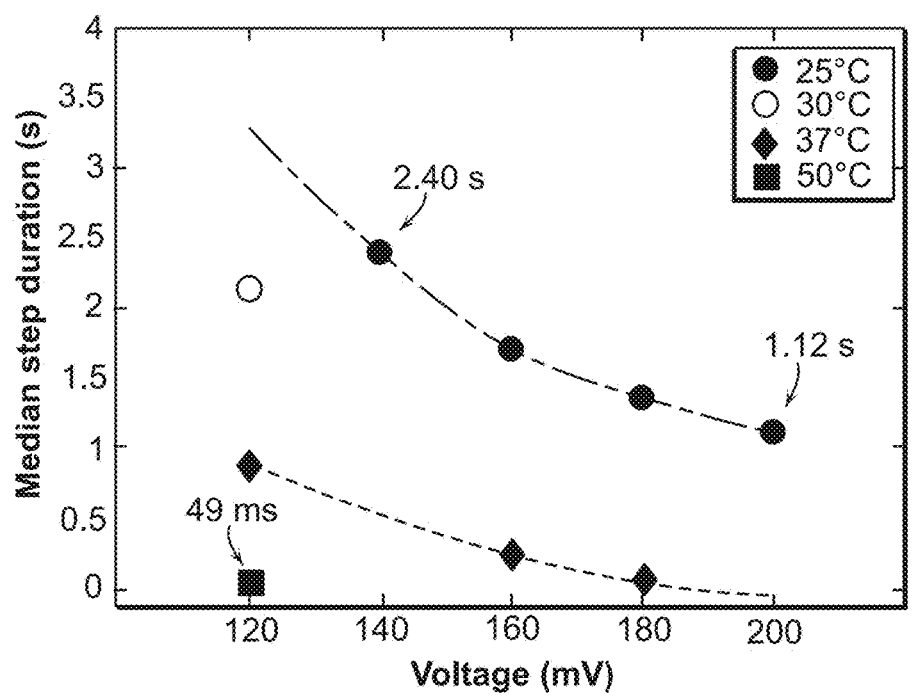
FIG. 13 is a plot of the median monomer step duration as a function of applied bias drive voltage with a T4 phase helicase clamp articulated DNA molecule for four different temperatures.

Because in the methodology provided herein for control pulsing involves the combination of a bias drive voltage, $V_{drive}$, plus a very brief interval of additional voltage control pulse, $V_{pulse}$, and\or a brief interval at a higher temperature in a thermal control pulse, $H_{pulse}$, there is provided herein an understanding of how higher voltage biases and higher temperatures affect stepping rates. Experimental results for these conditions were produced for voltage and temperature parameters for a condition without pulsing, again using a T4-helicase as an example of a clamp on a DNA strand. Referring to the plot of FIG. 12, absent ATP, when a DNA polymer with the bound clamp is driven through a nanopore by a constant cis to trans bias, the median duration of time it takes to step the full length of a polymer through a nanopore is shortened as the voltage bias, $V_{drive}$, across the nanopore, is increased. Referring also to FIG. 13, as a result, the median duration of the time interval between each monomer step—here termed median step duration—shortens as the voltage bias, $V_{drive}$, is increased, for the conditions representative of the data in the plot of FIG. 12, with a T4 helicase clamp. The median step duration data in the plot of FIG. 13 was determined for the data of FIG. 12 by dividing the measured duration of full molecule translocation shown in FIG. 12 by the number of monomers known to compose the full length of the translocated molecule.

Several other factors can influence the median step duration or time interval between each stop. For example, the addition of a low concentration of a non-hydrolysable analogue of ATP, 5'-(β,γ-imido) triphosphate (ADPNP), significantly reduces the range of duration times to completely traverse through the nanopore when many identical polymers are stepped through a nanopore as in the conditions represented by the plot of FIG. 11. Other factors that can affect the median step duration include the movement direction of a polymer through a clamp, e.g., the 3' to 5' direction or the 5' to 3' direction, as well as changes in the amino acid composition of the clamp, or formation of disulfide links between clamp components or other structures.

Referring again to FIG. 13, it is found that the temperature of the clamp and its immediate surroundings has a particularly striking effect on the median step duration as shown in the plotted data of FIG. 13. For example, using a T4 phage helicase as the clamp, while it is observed that lowering the temperature below room temperature can significantly lengthen the median step duration, increasing the temperature from 25° C. to 37° C. shortens the median step duration over three fold. Neither increased voltages nor increased temperatures were found to alter the precision with which the clamp steps monomer by monomer along the length of the observed DNA polymers.

Turning to embodiments of the voltage control pulses and thermal control pulses, it is to be recognized that the features of the nanopore system, the clamping component, and the duration and amplitude of the voltage and\or heat pulses of the methodology, are to be selected in coordination with each other and the other commonly used features of nanopore sensing known to those familiar with the methods of nanopore sensing and nanopore sequencing. In one embodiment, a strategy for implementing control pulses that produce deterministic stepping is as follows:

1) In a first step, set the constant bias drive voltage, $V_{drive}$, and all other conditions of the nanopore system such that the median step duration is as long as possible and so that the frequency of short-duration steps is as low as possible. Tins can be achieved, e.g., by setting the bias drive voltage, $V_{drive}$, to a voltage of between about 20 mV and about 140 mV and maintaining the reservoirs' solution medium at a temperature of between about 10° C. and about 15° C. It is to be recognized that although a longer median step duration may be achievable with a bias drive voltage, $V_{drive}$, that is at or below about 120 mV, a bias that is less than about 120 mV may not optimally prevent the passage of a duration of time during which a successive monomer unit could diffuse outside of the nanopore's sensing aperture region, as explained by Lu et al., Biophys. J., 109: 1439-1445, 2015, which is hereby incorporated by reference in its entirety. As explained below, such a condition would diminish the nanopore's ability to distinguish between the polymer's different subunits. As a result, in preferred embodiments, the bias drive voltage, $V_{drive}$, is at least about 120 mV, and in preferred embodiments is between about 120 mV and about 140 mV.

2) In a next step, set the frequency of the voltage control pulse, $V_{pulse}$, or the heat control pulse, $H_{pulse}$, or coincident control pulses of $V_{pulse}$ and $H_{pulse}$, such that the duration of time between pulses is significantly less than the duration of the shortest-duration stops that are measured to occur in the absence of pulses, with just the application of the bias drive voltage, $V_{drive}$. It is to be recognized that although the duration of time between pulses is preferably significantly less than the duration of the shortest-duration steps observed in the absence of pulses, the duration of time between pulses is preferably long enough to enable the nanopore system electronic to make an accurate evaluation of the ionic current flowing through the nanopore between each pulse. If the duration of time between pulses is sufficiently shorter than the duration of the shortest duration steps observed in the absence of pulses, then it will be guaranteed that the probability that the clamp will be driven to step stochastically by the bias voltage alone will become vanishingly small. Then, consequently, substantially every clamp step is due to the intentional application of a voltage control pulse, $V_{pulse}$, and\or a heat control pulse, $H_{pulse}$, and the polymer's stepping movement through the nanopore is guaranteed to be deterministic, controlled, and repeatable.

In other words, to assure that a target polymer advances through the nanopore with deterministic step-like motion, the duration of each voltage control pulse and\or thermal control pulse is selected to overcome the normal forces that bind the clamp to a monomer unit of a polymer for less than the length of time it takes the bias driving voltage, $V_{drive}$, to drive the polymer forward through the nanopore by one monomer unit.

Depending on a selected investigation to be conducted with the nanopore system, depending on the particulars of target polymers to be investigated, and depending on the availability of clamping components and appropriate nanopores, there are several preferred embodiments provided herein. Following are two embodiments that illustrate how a one skilled in the art of nanopore sensing and nanopore sequencing can select appropriate features of the system provided herein and how to set their parameters and those of the other commonly used features of nanopore sensing so that they are coordinated to work with each other. DNA will be used for the embodiments, but other charged polymers of linearly connected, i.e., sequential, monomer residues, such as RNA, proteins, and the molecules described above can be similarly probed with an appropriate clamping component reversibly bound to the polymer.

In various embodiments provided herein, single-stranded DNA (ssDNA), or double-stranded DNA (dsDNA) is the target polymer molecule. In either embodiment, the nanopore is configured with a limiting aperture through which only one strand of the target polymer will pass but through which this one strand with the bound clamping component cannot pass. Among readily available nanopores, either an organic nanopore, e.g., a protein, or an inorganic solid state nanopore, such as an aperture in a membrane, in either case having a channel aperture diameter that is less than the diameter of the clamp but greater than about 1 nm, is preferred for many embodiments.

The production, arrangement, and configuration of nanopores, membranes, and support structures of the nanopore system can be achieved in any suitable manner, e.g., as described in U.S. Pat. No. 9,617,591, to Moysey; as described in U.S. Pat. No. 7,468,271, to Golovchenko; as described in U.S. Pat. No. 8,698,481, to Lieber; as described in US 20120234679 to Garaj; as described in U.S. Pat. No. 9,702,849, to Lieber; as described in U.S. Pat. No. 9,611,140, to Russo; as described in U.S. Pat. No. 9,815,082 to Golovchenko; and as described in U.S. 20160231307, to Xie; the entirety of all of which are hereby incorporated by reference.

Embodiment With Example Parameters

For Counting Monomers Along a Target Polymer Length

In this example embodiment, there is specified a nanopore membrane formed from a lipid bilayer. For example, there can be employed a diPhPC lipid bilayer extending across an aperture in a support structure, with the support structure aperture having a diameter of between about 10 microns and about 20 microns. A suitable nanopore, e.g., a CsgG nanopore, can here be employed. Because it is known that a diPbPC lipid bilayer membrane can rupture at constant or long-duration voltage biases that are greater than about 300 mV, a relatively low bias driving voltage, e.g., $V_{drive}$=120 mV, is adequate here as the constant bias voltage to be maintained both during and between voltage control pulses, even though this relatively low bias voltage does not optimally diminish the length of time each successive monomer unit spends outside of the nanopore's most sensitive sensing aperture, as explained above.

With this driving voltage selected, then to assure that a target polymer advances through a CsgG nanopore in the diPhPC with deterministic step-like motion, the amplitude and duration of each voltage control pulse and\or thermal control pulse are selected to overcome the normal forces that bind the clamp to a monomer unit of a target polymer for less than the length of time it takes the bias driving voltage, $V_{drive}$, of 120 mV to drive the polymer forward through the nanopore by one monomer unit. The amplitude and duration of each voltage control pulse and\or thermal control pulse are also selected so as not to rupture or otherwise damage the membrane. Generally, for most embodiments, because the voltage control pulse is not constant, the voltage control pulse amplitude is larger than the amplitude of the constant driving voltage.

The relatively fragile diPhPC membrane can be ruptured by a constant voltage bias that is greater than about 180 mV, but can tolerate short, ~1 microsecond-duration, pulses that apply a voltage magnitude of up to about 500 mV. Thus, the voltage control pulses and\or thermal control pulses used to briefly overcome the forces that bind the clamping component to the polymer's monomer unit in the absence of ATP are in this example specified to be shorter than about 1 microsecond in duration and to have a voltage that is less than about 500 mV.

For this embodiment, the clamp can be implemented as any in a wide range of highly-processive DNA enzymes that bind to a single strand of DNA. For example, translocases such as helicases or polymerases can be used as the clamping component. Among helicases, many that bind to an unpaired single strand region of otherwise dsDNA are available, as explained by von Hippel et al., *Cell* 104: 177-190, 2001, hereby incorporated by reference in its entirety.

In this and various embodiments herein, it can be preferred to employ only one clamp rather than several clamps attached to the DNA polymer. As a result, a helicase that binds to an unpaired single strand DNA region is a well-suited clamp because those skilled in the art of molecular biology understand how to prevent multiple helicases from binding to a ssDNA sample by, for example, temporarily converting large portions of the ssDNA to dsDNA.

An SF1 family helicase, such as the T4 Dda helicase, can be a preferable clamp selection for this and many embodiments because the mode of translocation of the T4 Dda helicase along ssDNA 5' to 3' has been studied at high resolution and it is clear that most of the ca. 12-14 amino acid contacts these helicases make with bound DNA are with the sugar-phosphate back-bone of the DNA, as explained by Saikrishnan et. al., *Cell*, 137: 849-859, 2009, hereby incorporated by reference in its entirety. Consequently, it is understood herein that a SF1 family helicase binds equally well to all nucleobase sequences it encounters in a DNA strand to which it binds.

Furthermore, members of this family of translocates are found in many organisms and the force needed to slide the bound helicase along the DNA in the absence of ATP can vary significantly depending on the organism from which the SF1 family helicase is purified. For example, a clamp whose binding to DNA is not overcome by a constant bias voltage less than about 180 mV but whose binding to the DNA strand can be overcome by voltage pulses greater than about 200 mV, optionally coordinated with thermal pulses, both lasting for a duration less than about 500 μs, can be preferred.

To impose thermal control pulsing with or instead of voltage control pulsing, a 532 nm-wavelength laser operating at a beam energy of at least about 300 mW can be used in many embodiments. This laser raises the temperature of a volume of less than about 10 yoctoliters of ionic solution immediately surrounding the clamp to which one or more gold, silver or other light-absorbing nanoparticles have been bound, as explained above. The constant background temperature of the medium is preferably in this embodiment held at a bias temperature of about 15° C. and then is raised to about 50° C. by laser light that is emitted to temporally coincide with voltage control pulses.

The duration of time between voltage and/or heat control pulses is greater than shortest time required for monomer identification at the desired accuracy level but is less than the shortest time that is characteristic for sliding of the clamp one monomer unit under the conditions of the bias voltage, $V_{drive}$. This shortest measured time for sliding varies depending on which particular helicase is selected. For example, absent ATP, and with the preferred T4 Dda helicase as a clamp, it is found that time durations between steps that are less than 1 sec are extraordinarily rare when $V_{drive}=120$ mV. Thus, the interval between voltage control pulses can be set at or below 100 milliseconds, a condition that can be an easily implemented. This avoids undetected sliding due to the driving voltage, and thereby guarantees that the counted number of pulses that are applied to drive the entire length of a target DNA polymer through the nanopore will equal the number of monomer subunits. i.e., nucleobases, in the polymer length.

Embodiment With Example Parameters

For Determining Chemistry and Monomer Sequence

Along a Target Polymer Length

In a further embodiment, the nanopore system, clamp, and control pulses are selected to enable determination of the chemical nature of a target polymer and the sequence of monomer subunits along the target polymer. This embodiment, as above, considers the target polymer molecule DNA whose nucleobases are the monomer subunits of the polymer. Because more detailed information concerning the monomer subunits is asked here, a larger bias voltage to drive the polymer through the nanopore than those of the prior embodiment is required to minimize the effects of Brownian motion that would otherwise degrade detailed information. As a consequence, some of the parameters that are the subject of this embodiment and those of the other commonly used features of nanopore sensing are different than in the previous embodiment.

Because this embodiment requires a bias drive voltage, $V_{drive}$, that is larger than that of the previous embodiment, and therefore because the amplitude of the combined voltage of $V_{drive}+V_{pulse}$ is correspondingly larger than that of the previous embodiment, a less fragile, more robust membrane than that employed in the previous embodiment is here preferred. Appropriate membranes include a solid state membrane, such as a graphene membrane, a silicon nitride membrane, or other suitable solid state membrane, or an amphiphilic triblock copolymer membrane, as described by Zhao et al., *Science*, 279: 548-552, 1998, hereby incorporated by reference in its entirety, such as poly(dimethylsiloxane)-block-poly(2-methyloxazoline)-poly(dimethylsiloxane), or a mycolic acid membrane, as described by Langford et al., *J. Lipid Res.*, 52: 272-277, 2011, hereby incorporated by reference in its entirety, all of which can form more robust ion-impermeable membranes than a diPhPC lipid bilayer.

A membrane that extends across a relatively small aperture in a support structure, e.g., less than 20 micron-diameter support structure aperture, is also preferred because such is significantly more robust than are those formed across more conventional 10 micron-diameter—50 micron-diameter support structure apertures. A nanopore of a selected diameter, e.g., greater than 1 nm in diameter, or no more that about 2 nm in diameter, can be directly pierced through the membrane e.g., through a graphene membrane, or alternatively, a biological nanopore such as a mutant of the CsgG porin can be a preferred protein nanopore provided in the membrane. Either of these can more readily distinguish between the DNA nucleobases than α-hemolysin, as described by Howorka in US 20180148481, hereby incorporated by reference in its entirety.

A bias drive voltage, $V_{drive}$, of between about 140 mV and about 250 mV can here be preferred to minimize the number of monomers which contribute to each ionic current measurement by minimizing Brownian movement and by minimizing the length of time each successive monomer unit spends outside of the nanopore's most sensitive, narrow aperture, high electrical resistance region. This condition can be understood referring to FIGS. 14A-14C for an example drive voltage of about 120 mV. With the 120 mV drive voltage 38 imposed across the nanopore 20, such that one monomer unit 42 is disposed at the high-sensitivity site 44 of the nanopore, Brownian motion can fleetingly drive the monomer unit out of the high-sensitivity site, as shown in FIG. 14B. With the application of a larger bias driving voltage, e.g., greater than 125 mV, as shown in FIG. 14C, the subunit 42 is returned to the high-sensitivity site more rapidly, thereby improving monomer identification. Therefore, it can be preferred to either employ a relatively high bias drive voltage, greater than about 120 mV, or to employ a variable voltage that counteracts the Brownian motion.

To impose heat pulses in this embodiment, there can be employed, for example, a 532 nm-wavelength laser operating at a beam energy of at least about 300 mW, to raise the temperature of a volume of less than about 10 yoctoliters of the ionic solution immediately surrounding the clamp with a gold nanoparticle bound to the clamp or nanopore in the manner described above. The constant background temperature of the solution, preferably held to about 10° C., is raised to about 50° C. by laser light, and is controlled in the manner described above to coincide with voltage control pulses.

With a relatively robust membrane selected here across a support structure aperture diameter of less than about 10 microns, a constant voltage bias of greater than about 500 mV can rupture the membrane but voltage control pulses having a pulse duration that is at most between about 1 microsecond and about 3 microseconds and of magnitude less than about 900 mV can be tolerated. Thus, the voltage control pulses used to briefly overcome the forces that bind the clamping component to the polymer's monomer unit in the absence of ATP are here preferably shorter than about 3 microseconds in duration and are of a voltage magnitude that is less than about 900 mV.

An SF1 family helicase can be preferred in embodiments here because members of this family of translocases are found in many organisms and the force needed to slide the bound helicase along the DNA in the absence of ATP will vary significantly depending on the organism from which the SF1 family helicase is purified. For this example, a clamp whose binding to the DNA strand can be overcome by a control pulse duration of less than about 500 ns and magnitude of less than about 900 mV, but whose binding to DNA is not overcome by a bias drive voltage of less than about 500 mV can be preferred.

As in the previous embodiment, the duration of time between control pulses is here selected to be greater than shortest time required for monomer identification at the desired accuracy level but less than the shortest time that is known to be characteristic for sliding of the clamp under the conditions of the bias drive voltage alone. This shortest measured time for sliding will vary depending on which particular helicase is selected. Absent ATP and using the preferred SF1 family helicase as the clamp, the mean duration between slides is greater than about 100 ms and falls off exponentially such that sliding from one nucleobase to the next nucleobases under the condition of only a bias drive voltage of $V_{drive}$=300 mV occurs very rarely in a span of about 15 ms. Thus, setting the interval between voltage control pulses to occur at an easily-implemented duration of, e.g., between about 5 milliseconds and about 10 milliseconds minimizes stochastic sliding and provides deterministic stepping so as to assure that each successive nucleobases in the DNA sequence is detected and identified by its current signature at the nanopore.

Experimental Example

A MspA nanopore was provided in a diphytanoyl phosphatidylcholine membrane and arranged in a nanopore system as shown in FIG. 2. DNA with a Dda helicase clamp was loaded into the cis reservoir of the system, in an ionic solution of 1M KCl, 25 mM phosphate buffer, 2 mM ADPNP, 2 mM MgCl$_2$, at pH 8.0. The solution was held at 37° C. The bias driving voltage across the nanopore was 160 mV. Voltage control pulses were applied using the voltage pulse control system of FIG. 5 and the control methodology of FIG. 3. In a first experiment, the voltage control pulses were of duration 500 microseconds, and in a second experiment, the voltage control pulses were of duration 1 millisecond. The voltage control pulses were 300 mV in amplitude for both experiments. The nanopore current was measured and filtered at 2 kHz.

Figure 15A:
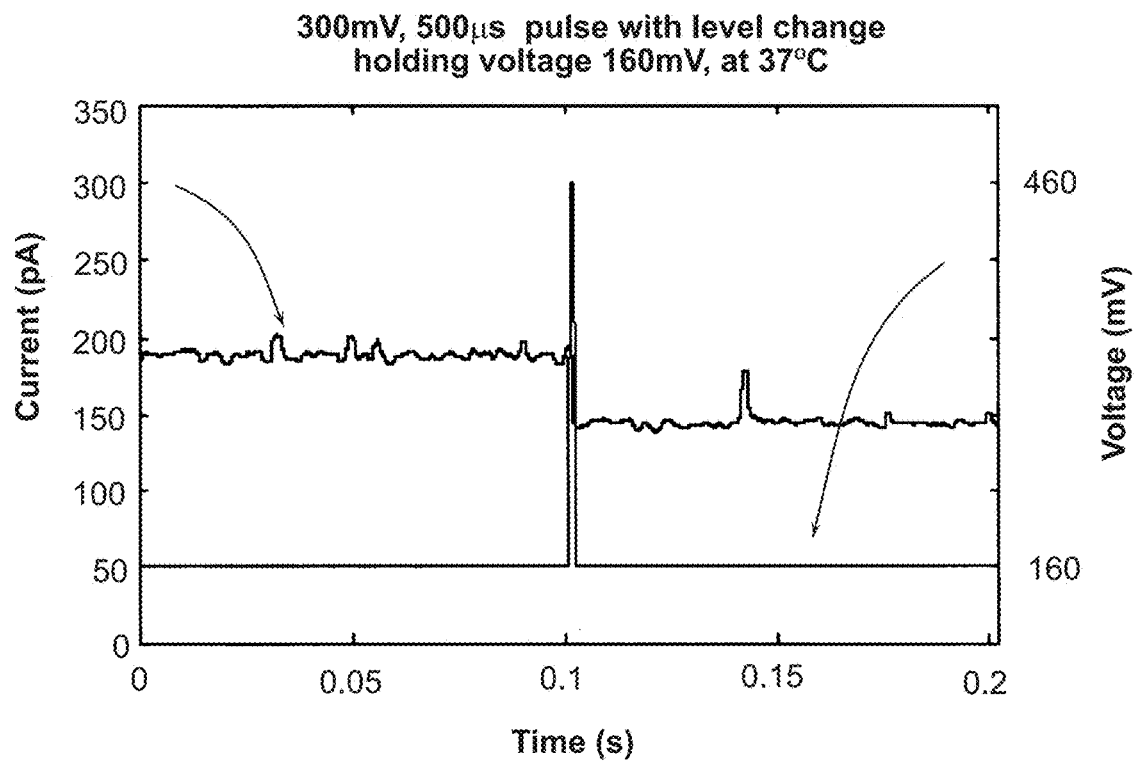
FIGS. 15A and 15B are plots of measured nanopore current and applied voltage control pulse amplitude as a function of time for an experimental nanopore system employing a 160 mV bias drive voltage.
Figure 15B:
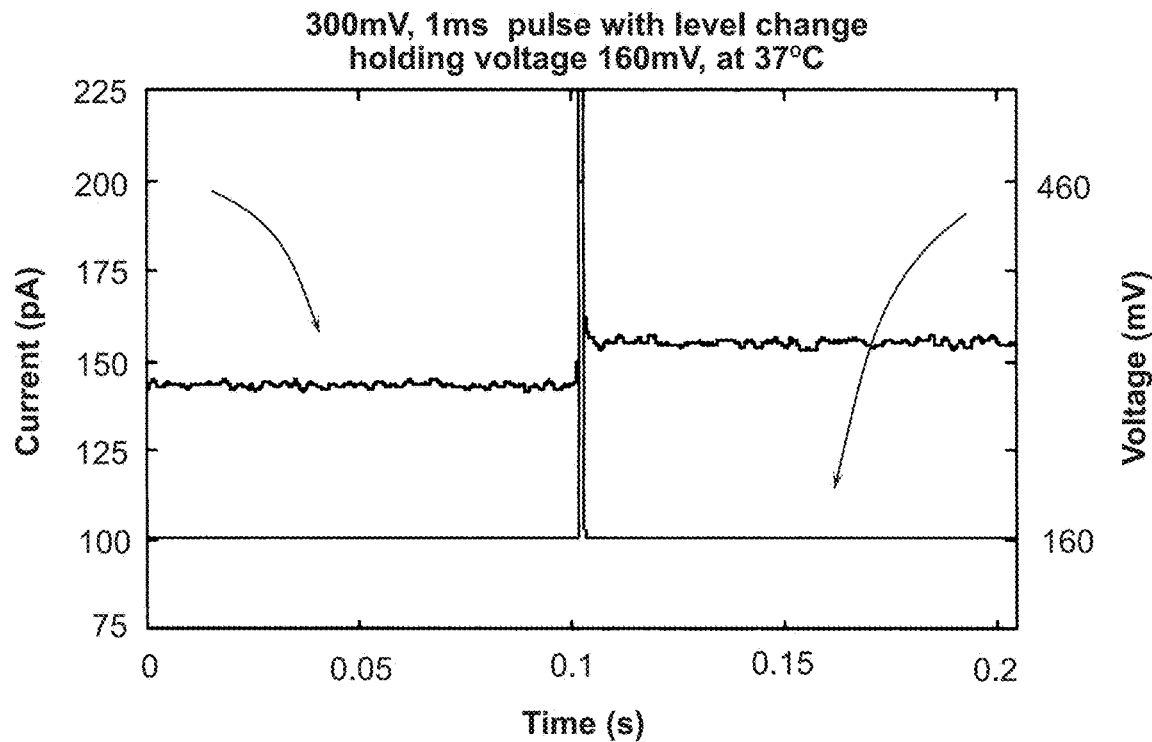

FIGS. 15A and 15B are plots of the nanopore current that was measured as a function of time as the voltage control pulses were applied, and show the applied voltage across the nanopore as a function of time, for the 500 microsecond-duration voltage control pulse and the 1 millisecond voltage control pulse, respectively. The measured nanopore ionic current is shown as the upper line and the axis is on the left of the plots, while the applied voltage pulse is shown as the lower line and its axis label is on the right of the plots. As shown in both plots of data, a measured change in the ionic current through the nanopore was coincident in time with an applied voltage control pulse, $V_{pulse}$. This indicates that the helicase clamp took a step of one monomer along the DNA strand length in response to one mono-applied voltage control pulse, $V_{pulse}$. The capacitive current spike over-shoot shown in the applied pulse in the plot of FIG. 15B is a consequence of inadequate compensation by the electronics during what was a relatively long-duration voltage control pulse of 1 millisecond.

With this description, the embodiments provided herein, and the experimental example, it is demonstrated deterministic stepping, rather than stochastic stepping, of a target polymer molecule translocation through a nanopore is achieved with the nanopore system, the clamp control, and the methodology provided herein, and enables the characterization of linearly connected, sequential, polymer subunits of a target polymer with a nanopore. Precise target polymer evaluation that has heretofore been difficult is thereby enabled.

It is to be understood that although preferred embodiments have been described in detail herein, it will be apparent to those skilled in the art that various modifications, additions, substitutions, and the like can be made without departing from the spirit of the invention, and these are therefore considered to be within the scope of the invention as defined in the claims which follow.

---

---

We claim:

1. A method for controlling translocation of a target polymer molecule through a nanopore, the target polymer molecule selected from nucleic acid polymer molecules and protein polymer molecules and including a sequential plurality of polymer subunits along a target polymer molecule length, comprising:
   reversibly binding an enzyme clamp to a plurality of sequential polymer subunits along the target polymer molecule length;
   disposing the target polymer molecule and reversibly bound clamp in an ionic solution that is in fluidic communication with the nanopore, the nanopore having an aperture diameter less than an outer diameter of the clamp;
   applying a constant translocation force across the nanopore to induce travel of the target polymer molecule in the ionic solution into the nanopore until the clamp on the target polymer molecule abuts the nanopore aperture and stops further travel of the target polymer molecule into the nanopore;
   applying a control pulse comprising at least one of a voltage control pulse across the nanopore and a thermal control pulse at the nanopore, the control pulse having a control pulse duration that steps the clamp along the target polymer molecule by no more than one polymer subunit in a direction opposite that of travel into the nanopore, with no fuel provided to the clamp, to step the target polymer molecule further into the nanopore by no more than one polymer subunit; and
   repeatedly applying the control pulse to cause a sequential plurality of polymer subunits of the target polymer molecule to translocate through the nanopore.

2. The method of claim 1 wherein applying a constant translocation force across the nanopore comprises applying at least one of electrophoretic force, hydrostatic pressure, optical force, and magnetic force.

3. The method of claim 1 wherein repeatedly applying the control pulse to cause a sequential plurality of polymer subunits to translocate through the nanopore comprises repeating application of the control pulse until the target polymer molecule length fully translocates through the nanopore.

4. The method of claim 1 further comprising a step of acquiring a representative indication of a polymer subunit as the polymer subunit translocates through the nanopore.

5. The method of claim 1 wherein the applied control pulse has a pulse duration that is less than a length of time required for the constant translation force to induce the target polymer molecule to travel into the nanopore by an additional polymer subunit.

6. The method of claim 1 wherein the constant translocation force comprises an electrostatic force imposed by application of a voltage bias across the nanopore, and wherein the control pulse comprises a voltage control pulse having a control pulse amplitude that is greater than a voltage bias amplitude applied across the nanopore.

7. The method of claim 1 wherein the control pulse comprises a thermal control pulse that is generated in the ionic solution at the nanopore by applying laser energy to a laser-energy absorptive material disposed at the nanopore.

8. The method of claim 1 wherein the applied control pulse duration is no greater than about one millisecond.

9. The method of claim 1 further comprising measuring current through the nanopore while a sequential plurality of polymer subunits of the target polymer molecule translocates through the nanopore.

10. The method of claim 1 wherein the clamp comprises a helicase.

11. A method for characterizing a target polymer molecule, the target polymer molecule selected from nucleic acid polymer molecules and protein polymer molecules and having polymer subunits along a target polymer molecule length, comprising:
   reversibly binding an enzyme clamp to a plurality of sequential polymer subunits along the target polymer molecule length;
   disposing the target polymer molecule and reversibly bound clamp in an ionic solution that is in fluidic communication with the nanopore, the nanopore having an aperture diameter less than an outer diameter of the clamp;
   applying a constant translocation force across the nanopore to induce travel of the target polymer molecule in the ionic solution into the nanopore until the clamp on the target polymer molecule abuts the nanopore aperture and stops further travel of the target polymer molecule into the nanopore;
   applying a control pulse comprising at least one of a voltage control pulse across the nanopore and a thermal control pulse at the nanopore, the control pulse having a control pulse duration that steps the clamp along the target polymer molecule by no more than one polymer subunit in a direction opposite that of travel into the nanopore, with no fuel provided to the clamp, to step the target polymer molecule further into the nanopore by no more than one polymer subunit;

acquiring a characteristic indication of a polymer subunit when the polymer subunit is in the nanopore; and repeatedly applying the control pulse to cause a sequential plurality of polymer subunits of the target polymer molecule to translocate through the nanopore into an ionic solution while acquiring a characteristic indication of each polymer subunit that translocates through the nanopore.

12. The method of claim 11 wherein a characteristic indication of a polymer subunit is acquired by measuring current flow through the nanopore when the polymer subunit is in the nanopore.

13. The method of claim 11 wherein repeatedly applying the control pulse comprises conducting one repetition of control pulse application after each acquisition of a characteristic indication of one polymer subunit in the sequential plurality of polymer subunits.

14. The method of claim 11 wherein acquiring a characteristic indication of a polymer subunit comprises at least one of counting the polymer subunit and identifying the polymer subunit.

15. The method of claim 11 wherein control pulse application and acquisition of a characteristic indication of a polymer subunit are repeated until the target polymer molecule length fully translocates through the nanopore.

16. The method of claim 15 wherein the acquisition of characteristic indications of sequential polymer subunits with repeated control pulse application comprises determining number of polymer subunits disposed along the target polymer molecule length.

17. The method of claim 15 wherein the acquisition of characteristic indications of sequential polymer subunits with repeated control pulse application comprises determining number of identical polymer subunits disposed along the target polymer molecule length.

18. The method of claim 11 wherein the constant translocation force comprises an electrostatic force imposed by application of a voltage bias across the nanopore, and wherein the control pulse comprises a voltage control pulse having a control pulse amplitude that is greater than a voltage bias amplitude applied across the nanopore.

19. The method of claim 11 wherein the control pulse comprises a thermal control pulse that is generated in the ionic solution at the nanopore by applying laser energy to a laser-energy absorptive material disposed at the nanopore.

20. The method of claim 11 wherein applying a constant translocation force across the nanopore comprises applying at least one of electrophoretic force, hydrostatic pressure, optical force, and magnetic force.

21. A nanopore system for characterizing a target polymer molecule selected from nucleic acid polymer molecules and protein polymer molecules and including a sequential plurality of polymer subunits along a target polymer molecule length, comprising:

a first fluidic reservoir and a second fluidic reservoir, the first and second fluidic reservoirs in fluidic communication with a nanopore that forms a sole fluidic path between the first fluidic reservoir and the second fluidic reservoir;

an enzyme clamp provided in the first fluidic reservoir, the clamp abutting the nanopore and reversibly bound to a sequential plurality of polymer subunits of the target polymer molecule in ionic solution in the first fluidic reservoir;

a circuit comprising an electrode in the first reservoir, an electrode in the second reservoir, and a current amplifier for applying a constant voltage bias across the nanopore, between the first reservoir and the second reservoir to induce travel of the target polymer molecule into the nanopore;

a voltage pulse generator connected to the circuit to apply voltage control pulses across the nanopore, between the first reservoir and the second reservoir, to step the clamp along sequential polymer subunits of the target polymer molecule, polymer subunit by polymer subunit, in a direction away from the nanopore, and step the polymer molecule further into the nanopore, the system including no fuel for the clamp and no source of fuel for the clamp; and a computer controller connected to the circuit to collect an electrical indication of ionic current through nanopore while a sequential plurality of polymer subunits of the target polymer molecule steps through the nanopore.

22. The nanopore system of claim 21 wherein the nanopore comprises a biological nanopore.

23. The nanopore system of claim 22 wherein the nanopore comprises a CsgG nanopore.

24. The nanopore system of claim 22 wherein the nanopore comprises a biological nanopore in a lipid bilayer.

25. The nanopore system of claim 22 wherein the nanopore comprises an nanopore in a solid state membrane.

26. The nanopore system of claim 25 wherein the solid state membrane comprises graphene.

27. The nanopore system of claim 21 further comprising:

a laser connected to the computer controller to produce laser pulses;

optics disposed adjacent to the laser and oriented to direct the laser pulses to the nanopore; and a material element, disposed at the nanopore, that is absorptive of energy from the laser pulses to heat the ionic solution during each laser pulse.

28. A nanopore system for characterizing a target polymer molecule selected from nucleic acid polymer molecules and protein polymer molecules and including a sequential plurality of polymer subunits along a target polymer molecule length, comprising:

a first fluidic reservoir and a second fluidic reservoir, the first and second fluidic reservoirs in fluidic communication with a nanopore that forms a sole fluidic path between the first fluidic reservoir and the second fluidic reservoir;

an enzyme clamp provided in the first fluidic reservoir abutting the nanopore and being reversibly bound to a sequential plurality of polymer subunits of the target polymer molecule;

a circuit comprising an electrode in the first reservoir, an electrode in the second reservoir, and a current amplifier for applying a constant voltage bias across the nanopore, between the first reservoir and the second reservoir to induce travel of the target polymer molecule into the nanopore;

a laser connected to the computer controller to produce laser pulses;

optics disposed adjacent to the laser and oriented to direct the laser pulses to the nanopore;

a material element, disposed at the nanopore, that is absorptive of energy from the laser pulses to heat the ionic solution during each laser pulse and in turn to step the clamp along sequential polymer subunits of the target polymer molecule, polymer subunit by polymer subunit, in a direction away from the nanopore, and to step the target polymer molecule further into the nanopore, the system including no fuel for the clamp and no source of fuel; and a computer controller connected to the circuit to collect electrical indications of ionic current through nanopore while the sequential plurality of polymer subunits of the target polymer molecule steps through the nanopore.

29. The nanopore system of claim 28 wherein the material element comprises a nanoparticle consisting of one of a gold nanoparticle and a silver nanoparticle.

30. The nanopore system of claim 29 wherein the nanoparticle is linked to at least one of the clamp and the nanopore.

* * * * *